US012661126B2

(12) United States Patent
Kawamura et al.

(10) Patent No.: US 12,661,126 B2
(45) Date of Patent: Jun. 23, 2026

(54) HEMOSTATIC DEVICE

(71) Applicant: TERUMO KABUSHIKI KAISHA,
Tokyo (JP)

(72) Inventors: Tomoya Kawamura, Aliso Viejo, CA
(US); Tatsuya Ouchi, Fujinomiya (JP);
Koki Yamashita, Fuji (JP); **Yuna
Hidaka**, Moriya (JP)

(73) Assignee: TERUMO KABUSHIKI KAISHA,
Tokyo (JP)

( * ) Notice: Subject to any disclaimer, the term of this
patent is extended or adjusted under 35
U.S.C. 154(b) by 232 days.

(21) Appl. No.: 18/507,576

(22) Filed: Nov. 13, 2023

(65) Prior Publication Data

US 2024/0074767 A1      Mar. 7, 2024

Related U.S. Application Data

(63) Continuation of application No.
PCT/JP2022/020039, filed on May 12, 2022.

(30) Foreign Application Priority Data

May 14, 2021    (JP) ................................. 2021-082259

(51) Int. Cl.
*A61B 17/135*        (2006.01)
*A61B 17/12*         (2006.01)

(52) U.S. Cl.
CPC ....................... *A61B 17/135* (2013.01); *A61B
2017/12004* (2013.01)

(58) Field of Classification Search
CPC .............. A61B 17/132; A61B 17/1325; A61B
17/1327; A61B 17/135; A61B 17/1355;
A61B 2017/12004
See application file for complete search history.

(56) References Cited

U.S. PATENT DOCUMENTS

2012/0116444 A1*  5/2012  Zodnik ................ A61B 17/135
606/202
2015/0018868 A1*  1/2015  Pancholy ........... A61B 17/1325
606/202

(Continued)

FOREIGN PATENT DOCUMENTS

JP          2020116314 A      8/2020
JP          2021502220 A      1/2021

(Continued)

OTHER PUBLICATIONS

International Search Report (PCT/ISA/210) with English translation
and Written Opinion (PCT/ISA/237) mailed on Jul. 12, 2022, by the
Japanese Patent Office as the International Searching Authority for
International Application No. PCT/JP2022/020039.

(Continued)

*Primary Examiner* — Tan-Uyen T Ho
*Assistant Examiner* — Lindsey Bachman
(74) *Attorney, Agent, or Firm* — .Buchanan Ingersoll &
Rooney PC

(57) ABSTRACT

A hemostatic device that includes: a pressing member con-
figured to compress the puncture site; and a first band, a
second band, and a third band configured to be connected to
the pressing member. The pressing member includes a
pressing portion configured to compress the puncture site
and a support member configured to fix the pressing portion.
The support member has a first region in which the pressing
portion is located, and a second region which is located
outside the first region and to which the first band, the
second band, and the third band are connectable. The first
band and the second band have a center point in the first
region when the first band and the second band slide in a
state of being connected to the second region. The support (Continued)

100 member includes a projection protruding toward the pressing portion on a third band side of the first region.

8 Claims, 23 Drawing Sheets

(56)                    References Cited

U.S. PATENT DOCUMENTS

| | | | |
|---|---|---|---|
| 2018/0008281 A1* | 1/2018 | Hazama | A61B 17/135 |
| 2018/0014831 A1* | 1/2018 | Salimi | A61B 17/135 |
| 2019/0133602 A1 | 5/2019 | Kiemeneij et al. | |
| 2021/0145451 A1 | 5/2021 | Watanabe et al. | |

FOREIGN PATENT DOCUMENTS

| | | | | |
|---|---|---|---|---|
| WO | WO-2015008240 A1 * | 1/2015 | ......... | A61B 17/1325 |
| WO | 2019090104 A2 | 5/2019 | | |
| WO | 2020027123 A1 | 2/2020 | | |

OTHER PUBLICATIONS

English Translations of the International Search Report (Form PCT/ISA/210) and the Written Opinion of the International Searching Authority (Form PCT/ISA/237) issued Jul. 12, 2022, by the Japan Patent Office in corresponding International Application No. PCT/JP2022/020039. (5 pages).

* cited by examiner

100

FIG. 13A
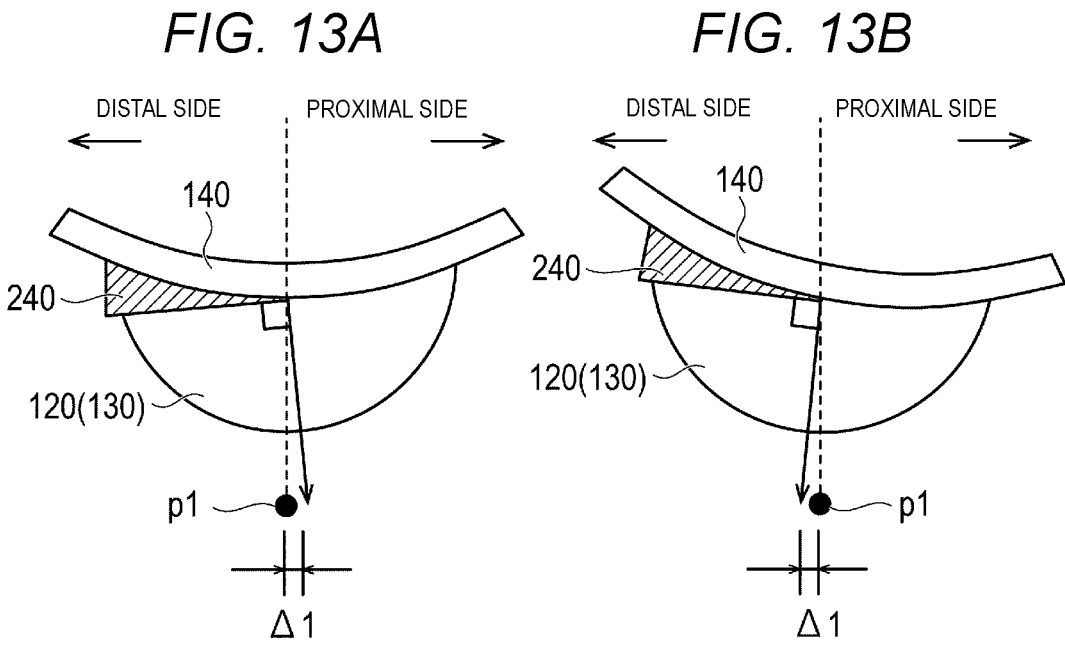
FIG. 13B
FIG. 13C
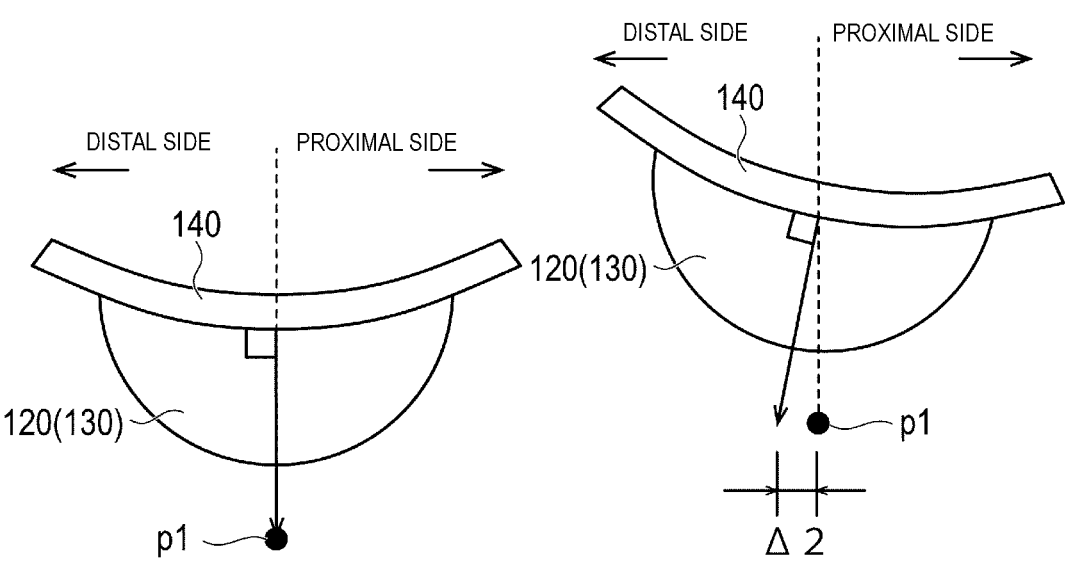
FIG. 13D

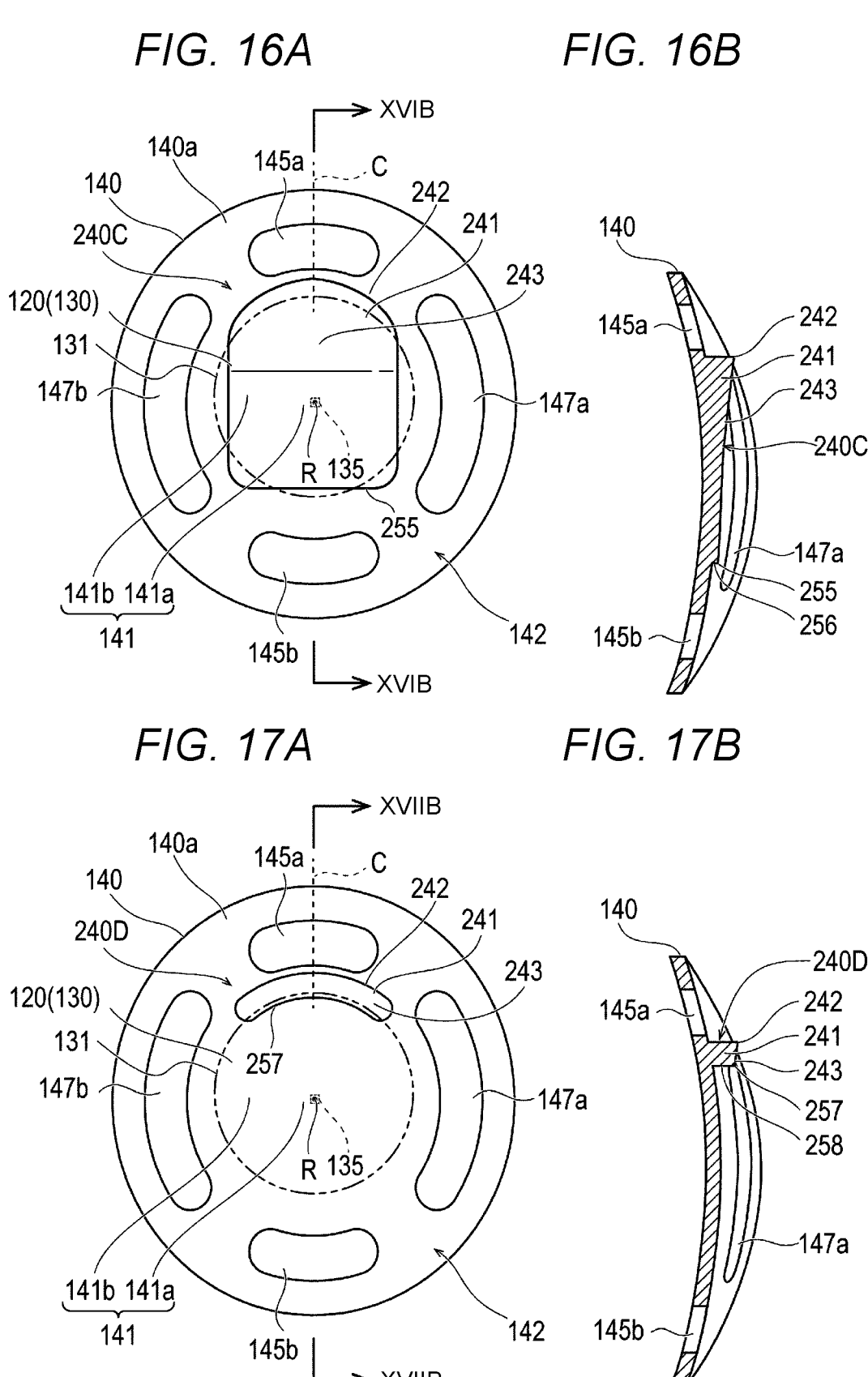
*FIG. 16A*          *FIG. 16B*
*FIG. 17A*          *FIG. 17B*

HEMOSTATIC DEVICE

CROSS-REFERENCES TO RELATED APPLICATIONS

This application is a continuation of International Application No. PCT/JP2022/020039 filed on May 12, 2022, which claims priority to Japanese Application No. 2021-082259 filed on May 14, 2021, the entire content of both of which is incorporated herein by reference.

TECHNOLOGICAL FIELD

The present disclosure generally relates to a hemostatic device.

BACKGROUND DISCUSSION

As one of catheter procedures, a procedure is known in which various elongated medical devices are introduced into a blood vessel through a puncture site formed by puncturing the blood vessel in an arm or a hand of a patient to perform a procedure and a therapy at a lesion site. For example, International Patent Application Publication No. WO2019/090104 discloses a hemostatic device that stops bleeding of a puncture site formed to enable access to a blood vessel (including a distal radial artery) running in a hand.

The hemostatic device in International Patent Application Publication No. WO2019/090104 includes a pressing member that applies a compressive force to a puncture site formed in a hand of the patient, a plurality of bands that fix the pressing member to the hand of the patient, and a support member that is disposed on the bands and presses the pressing member against the hand of the patient. The plurality of bands include a band that is wrapped along an external periphery of the hand, and a band that is disposed in an interdigital portion located between adjacent fingers of the hand.

An operator such as a doctor (hereinafter, referred to as "operator") disposes the pressing member and the support member so as to overlap the puncture site formed in the hand of the patient when stopping bleeding of the puncture site using the hemostatic device in International Patent Application Publication No. WO2019/090104. The operator wraps a band around the external periphery of the hand, and further disposes the band in the interdigital portion between a thumb and a forefinger. The operator can prevent the pressing member from being deviated from the puncture site formed in the hand of the patient by fixing the hemostatic device using each band in a state where the pressing member is disposed at the puncture site formed in the hand of the patient and in a peripheral portion of the puncture site.

However, the hemostatic device disclosed in International Patent Application Publication No. WO2019/090104 may have the following problems.

In the hemostatic device in International Patent Application Publication No. WO2019/090104, when the band is wrapped around the hand of the patient in a state where the pressing member is disposed on the hand of the patient, a gap exists between the support member and the hand depending on a physique or a puncture position of the patient, and the band may not fit along the external periphery of the hand of the patient. In such a state, the pressing member and the support member can be firmly fixed to the hand of the patient by strongly tightening the band for finger hooking of the hemostatic device in International Patent Application Publication No. WO2019/090104. Meanwhile, in such a case, since it is necessary to strongly tighten the band, pain may occur in the patient. Therefore, in the hemostatic device in International Patent Application Publication No. WO2019/090104, when the band cannot be strongly tightened due to pain or the like of the patient, the support member is disposed in a state of being inclined in a direction approaching a surface of the hand from a fingertip side to a forearm portion side of the hand. In the hemostatic device in International Patent Application Publication No. WO2019/090104, when the support member is disposed as described above, the pressing member cannot apply a compressive force to the puncture site in a vertical direction. Accordingly, the hemostatic device in International Patent Application Publication No. WO2019/090104 cannot effectively apply a compressive force to the puncture site.

SUMMARY

A hemostatic device is disclosed, which is capable of effectively applying a compressive force to a puncture site.

A hemostatic device according to the disclosure includes: a pressing member configured to compress a puncture site formed in a patient; a first band configured to be connected to the pressing member; a second band configured to be connected to the pressing member; and a third band configured to be connected to the pressing member. The pressing member includes a pressing portion configured to compress the puncture site and a support member configured to fix the pressing portion. The support member has a first region in which the pressing portion is located, and a second region which is located outside the first region and to which the first band, the second band, and the third band are connectable. The first band and the second band have a center point that is a center in the first region when the first band and the second band slide in a state of being connected to the second region, and the first band and the second band slide around the pressing portion in the second region about the center point. The third band extends in a different direction from the first band and the second band in a state where the third band is connected to the second region, and is configured to be disposed between fingers of the patient. The support member includes a projection protruding toward the pressing portion on a third band side of the first region.

According to the hemostatic device of the disclosure, the first band and the second band can slide around the center point located in the first region of the support member in a state where the first band and the second band are connected to the second region. Therefore, the hemostatic device can adjust angles and positions of the two bands relative to a hand of a patient by sliding the two bands around the pressing portion with the pressing portion as the center while disposing the pressing member at the puncture site formed in the hand of the patient. By adjusting the angles and positions of the first band and the second band, the operator can suitably attach the hemostatic device to a patient in accordance with a physique and a puncture position of the patient while disposing the pressing member at the puncture site formed in the hand of the patient. When both the first band and the second band are located on a wrist side of the patient, a side of the support member to which the third band is connected may lift up. Since the hemostatic device of the disclosure includes the projection protruding toward the pressing portion on the third band side of the first region of the support member, a compressing direction of the pressing portion is directed to a direction toward the puncture site with a limited amount of deviation from a direction toward the puncture site. Accordingly, the hemostatic device can be suitably attached to the patient in accordance with the physique and the puncture position of the patient, and the compressive force can be effectively applied to the puncture site.

A hemostatic device according to the disclosure includes: a pressing member configured to compress a puncture site formed in a patient; a first band configured to be connected to the pressing member; a second band configured to be connected to the pressing member; a third band configured to be connected to the pressing member; the pressing member including an inflatable member configured to compress the puncture site and a support member configured to fix the pressing portion; the support member including a first region in which the pressing portion is located, and a second region which is located outside the first region and to which the first band, the second band, and the third band are connectable; the third band extending in a different direction from the first band and the second band in a state where the third band is connected to the second region; and wherein the support member includes a projection protruding toward the pressing portion on a third band side of the first region.

A method is disclosed for attaching a hemostatic device for compressing a puncture site formed in a patient, the method includes: positioning a pressing portion on a support member of the hemostatic device over the puncture site formed in the patient; and attaching the pressing portion on the support member of the hemostatic device to the patient with a first band, a second band, and a third band, the third band extending in a different direction from the first band and the second band and wherein the support member includes a projection protruding toward the pressing portion on a third band side of the support member.

BRIEF DESCRIPTION OF THE DRAWINGS

FIGS. 13A and 13B are schematic views used to show operations of an embodiment in which the support member includes the projection.

FIGS. 13C and 13D are schematic views used to show operations of a comparative example in which the support member does not include the projection.

FIG. 14A is a plan view of the support member according to a first modification viewed from the one surface side on which the pressing portion is disposed.

FIG. 14B is a cross-sectional view taken along a line XIVB-XIVB in FIG. 14A.

FIG. 15A is a plan view of the support member according to a second modification viewed from the one surface side on which the pressing portion is disposed.

FIG. 15B is a cross-sectional view taken along a line XVB-XVB in FIG. 15A.

FIG. 16A is a plan view of the support member according to a third modification viewed from the one surface side on which the pressing portion is disposed.

FIG. 16B is a cross-sectional view taken along a line XVIB-XVIB in FIG. 16A.

FIG. 17A is a plan view of the support member according to a fourth modification viewed from the one surface side on which the pressing portion is disposed.

FIG. 17B is a cross-sectional view taken along a line XVIIB-XVIIB in FIG. 17A.

DETAILED DESCRIPTION

Figure 1:
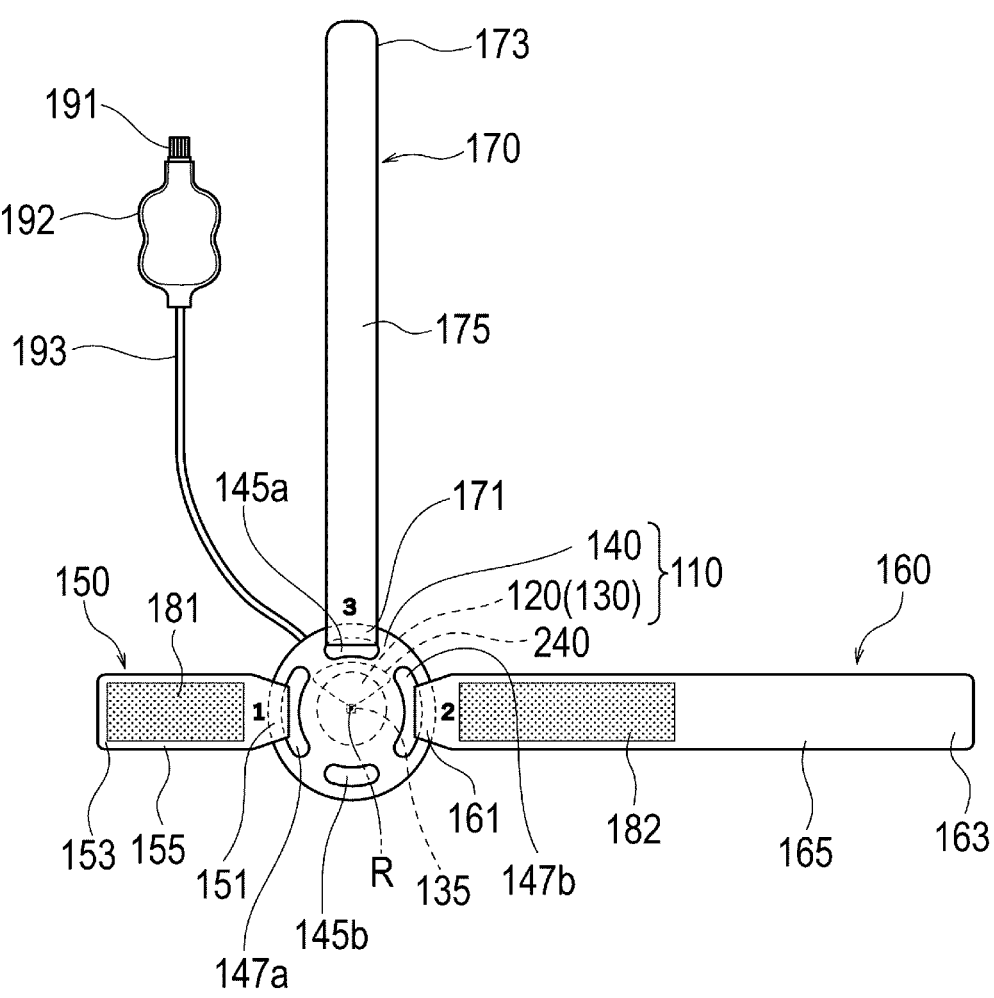
FIG. 1 is a plan view showing a hemostatic device according to an embodiment, viewed from an outer surface side of each band.

Set forth below with reference to the accompanying drawings is a detailed description of embodiments of a hemostatic device. The following description does not limit the technical scope or the meaning of terms described in the claims. Dimensional ratios in the drawings are exaggerated for convenience of illustration and may differ from actual ratios.

FIGS. 1 to 13D are views showing a hemostatic device 100 according to the present embodiment. FIGS. 14A to 20B are views showing modifications of a support member. FIGS. 21 to 28 are views showing usage examples of the hemostatic device 100.

For example, as shown in FIGS. 21 and 24 to 28, the hemostatic device 100 can be used to stop bleeding of a puncture site (for example, each of puncture sites p1 and p2 to be described later) formed in a hand H located on a distal side (finger side) of a forearm portion A of a patient when a sheath tube of an introducer 200 indwelt in the puncture site is removed.

Although a specific position of the puncture site as a hemostasis target of the hemostatic device 100 is not particularly limited, the following first puncture site p1 and second puncture site p2 are illustrated in the present embodiment. In the present specification, a structure of each part of the hemostatic device 100 will be mainly described through an example of using the hemostatic device 100 to stop bleeding of the first puncture site p1.

Figure 21:
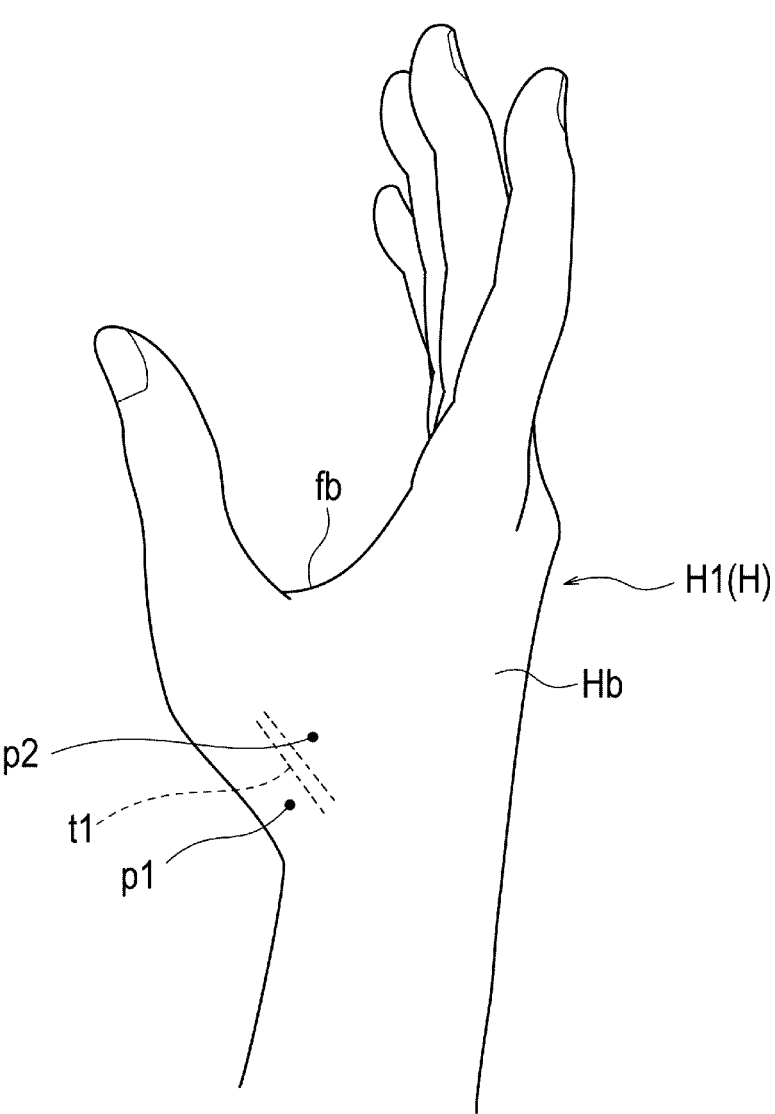
FIG. 21 is a view showing a hand (right hand) of a patient to whom the hemostatic device is to be used.
Figure 24:
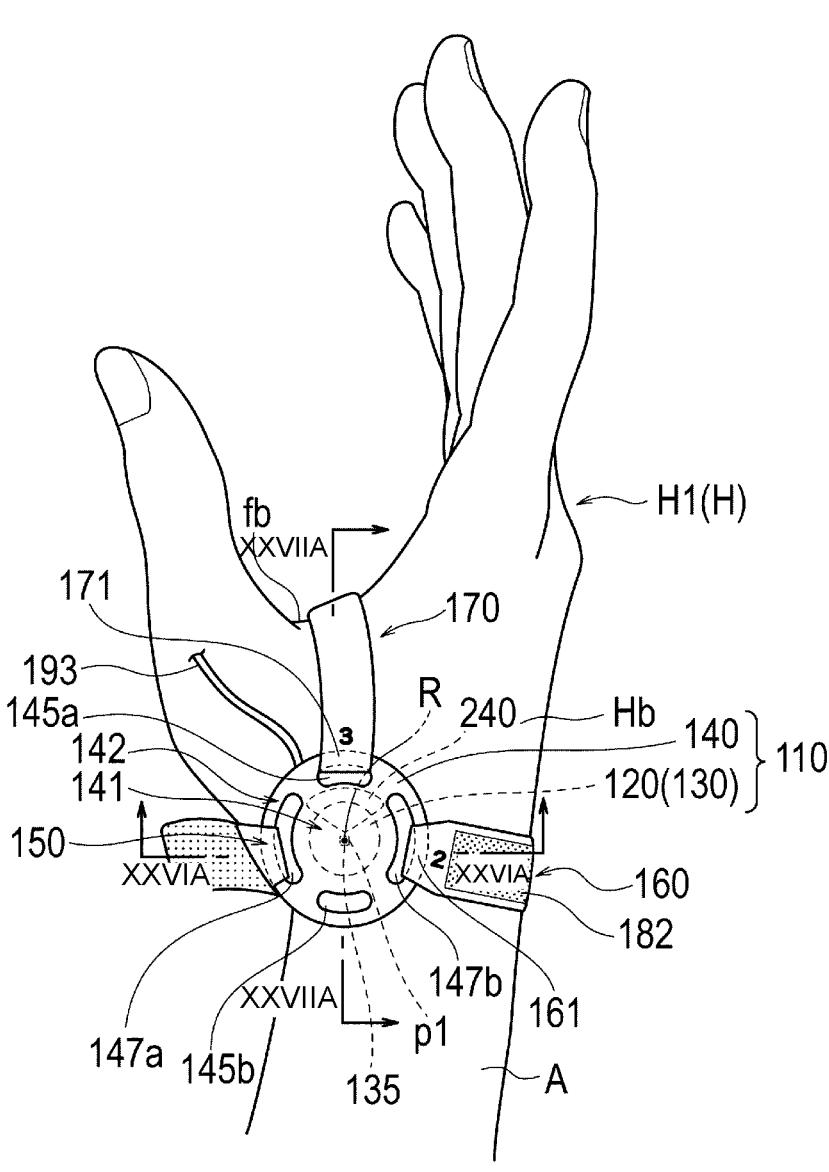
FIG. 24 is a view schematically showing the first usage example of the hemostatic device.

As shown in FIGS. 21 and 24, the first puncture site p1 is a puncture site formed in an artery B (hereinafter also referred to as "blood vessel B") located in a snuff box of a palmar artery running on a dorsal Hb side of a right hand H1 (hand H) located on the distal side of the forearm portion A of the patient. The snuff box is a hollow of the hand located near a radius when the patient spreads a thumb of the hand H.

Figure 28:
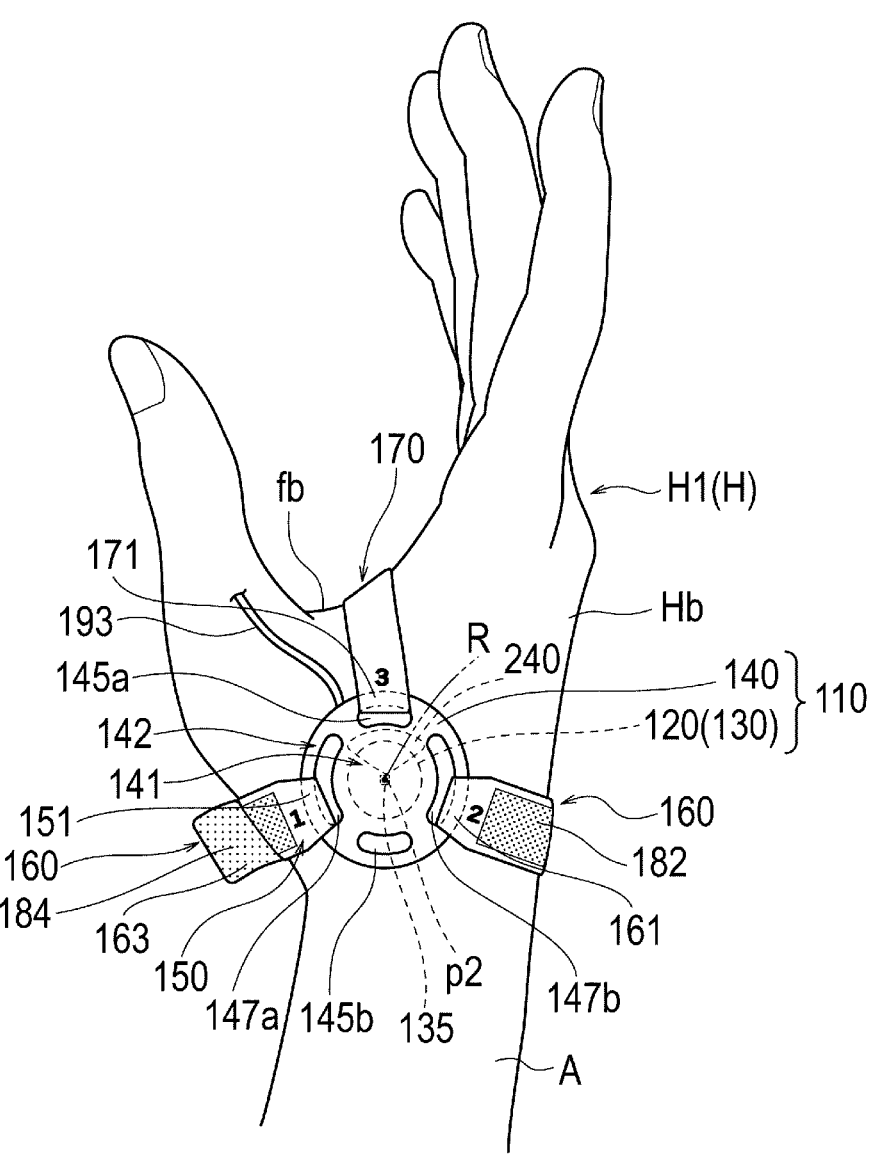
FIG. 28 is a view schematically showing a second usage example of the hemostatic device.

As shown in FIGS. 21 and 28, the second puncture site p2 is a puncture site formed in a distal radial artery located on a distal side of the snuff box of the palmar artery running on dorsal Hb side of the right hand H1 of the patient. The second puncture site p2 is located on a distal side of the right hand H1 relative to the first puncture site p1 with reference to an extensor pollicis longus muscle tendon t1 located on the dorsal Hb side of the right hand H1 of the patient.

Hereinafter, the hemostatic device 100 will be described in detail.

As shown in FIGS. 1, 2, 24, 26, and 27, the hemostatic device 100 generally includes a pressing member 110 configured to compress the first puncture site p1 formed in the right hand H1 of the patient, a third band 170 configured to be connected to the pressing member 110, a first band 150 configured to be connected to the pressing member 110, and a second band 160 configured to be connected to the pressing member 110. As shown in FIGS. 1, 2, 24, 26, and 27, the third band 170, the first band 150, and the second band 160 are connected to the pressing member 110. Specifically, in FIGS. 1, 2, 24, 26, and 27, the first band 150, the second band 160, and the third band 170 are connected to the pressing member 110 via a plurality of hole portions (first hole portion 145*a* and second hole portions 147*a* and 147*b*) in a second region 142 of a support member 140.

Figure 8:
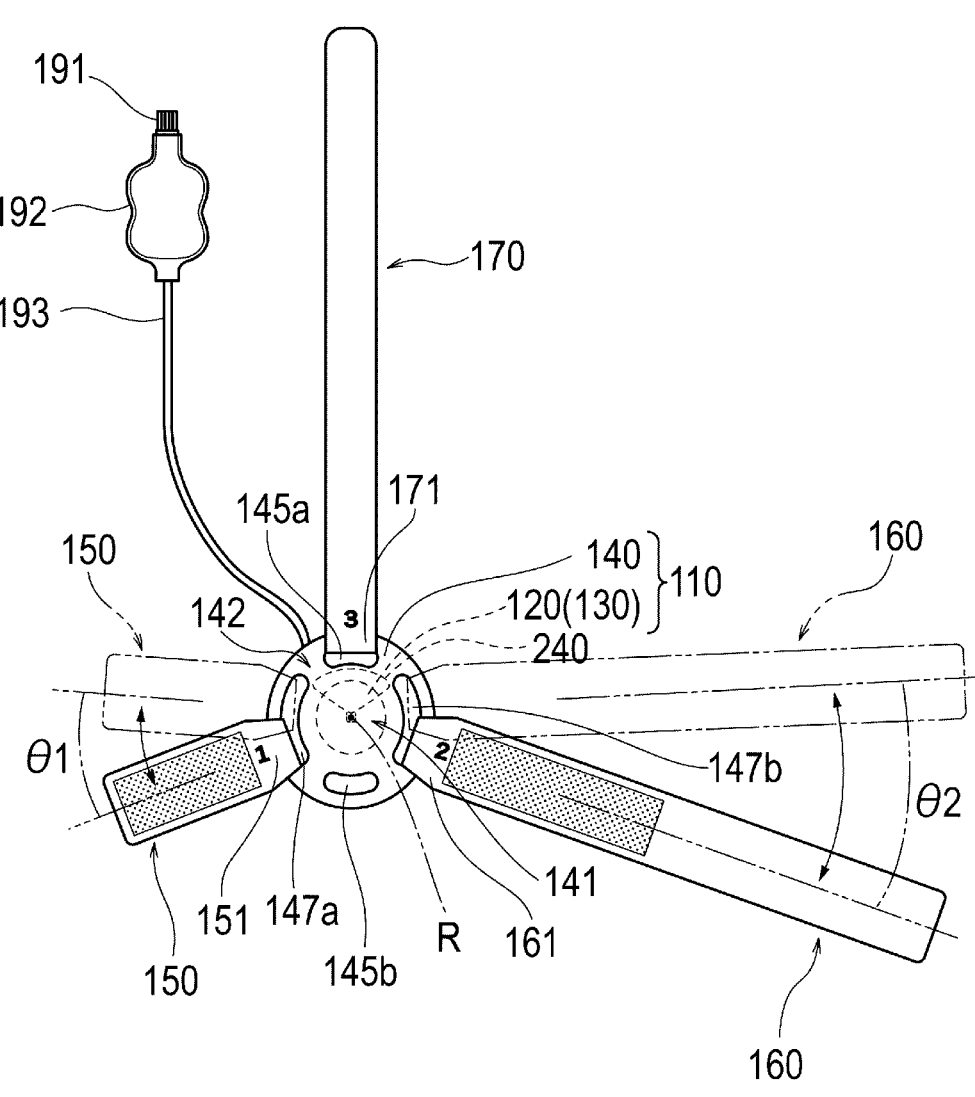
FIG. 8 is a plan view of the hemostatic device viewed from the outer surface side of each band, and shows states before and after a first band and a second band connected to a pressing member are slid.
Figures 9, 10:
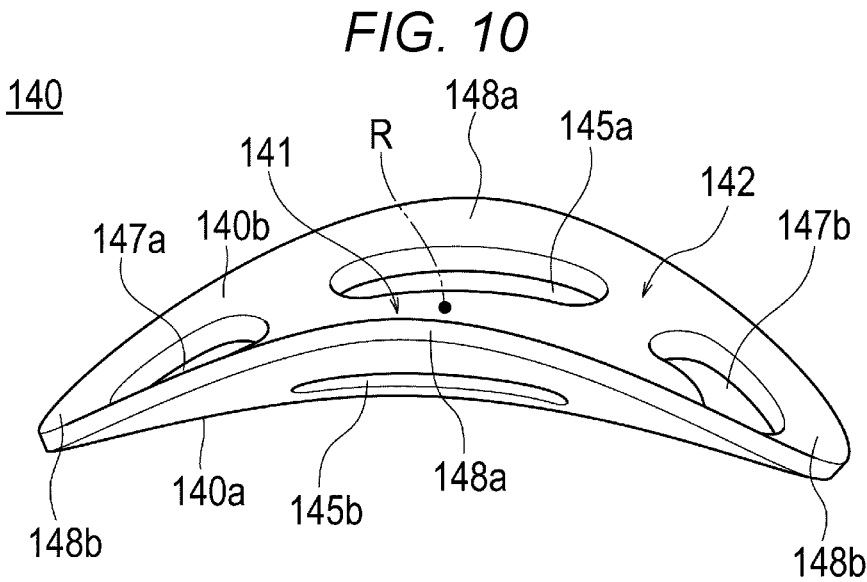
FIG. 9 is a perspective view of a support member in the pressing member.
FIG. 10 is a perspective view of the support member in the pressing member.

In the hemostatic device 100, as to be described later, among the three bands which are the third band 170, the first band 150, and the second band 160, the two bands which are the first band 150 and the second band 160 are configured to be slid around a pressing portion 120 in the second region 142 about the pressing portion 120. A center point R, which is a center when the first band 150 and the second band 160 slide, is located in a first region 141. Therefore, the first band 150 and the second band 160 are configured to slide around the pressing portion 120 in the second region 142 about the center point R located in the first region. In FIG. 8, the hemostatic device 100 is configured such that the two bands which are the first band 150 and the second band 160 are slidable around the pressing portion 120 along the hole portions 147*a* and 147*b* about the pressing portion 120. Accordingly, the two bands, which are the first band 150 and the second band 160, can be disposed at different angles in a radial shape about the center point R in the first region 141.

As shown in FIG. 24, when the hemostatic device 100 is attached to the right hand H1 of the patient, the third band 170 can be hooked on an interdigital portion fb located between two adjacent fingers (for example, thumb and forefinger).

Figure 5:
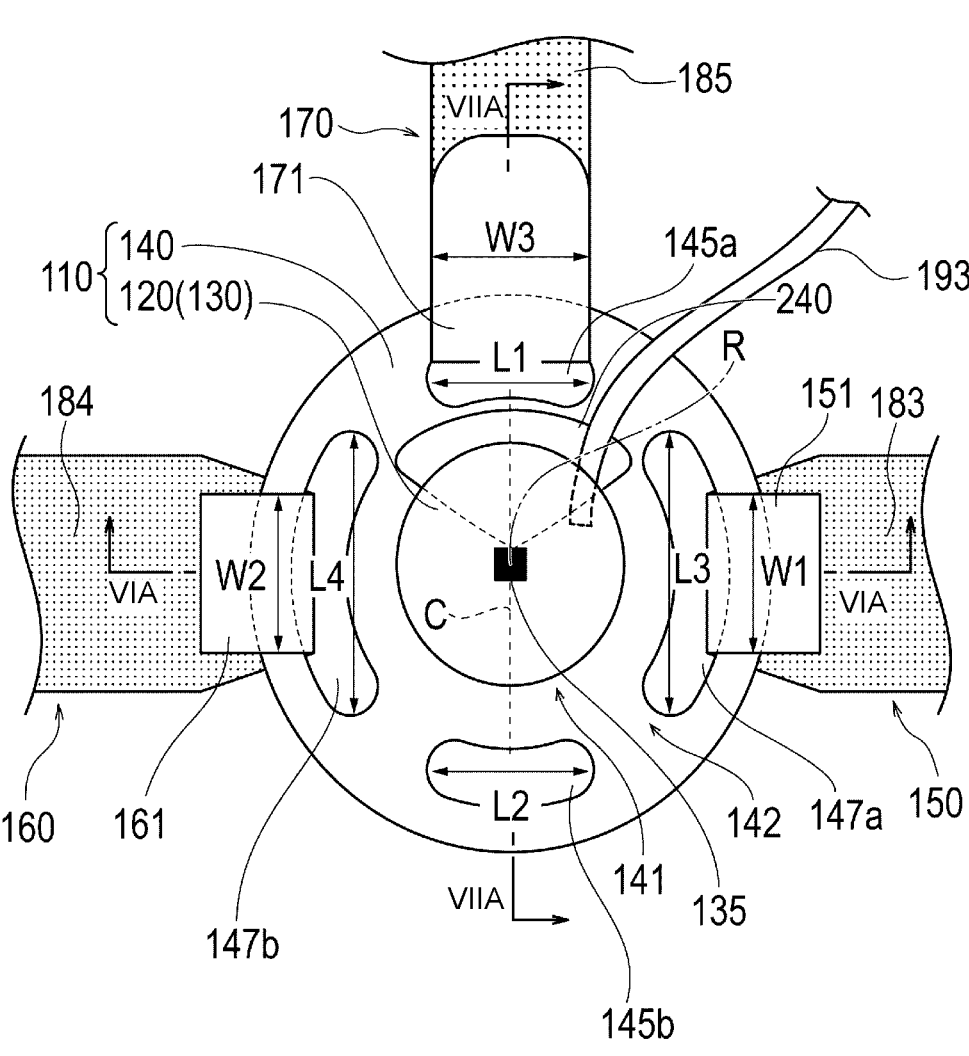
FIG. 5 is an enlarged plan view of a part of the hemostatic device viewed from the inner surface side of each band.
Figure 22:
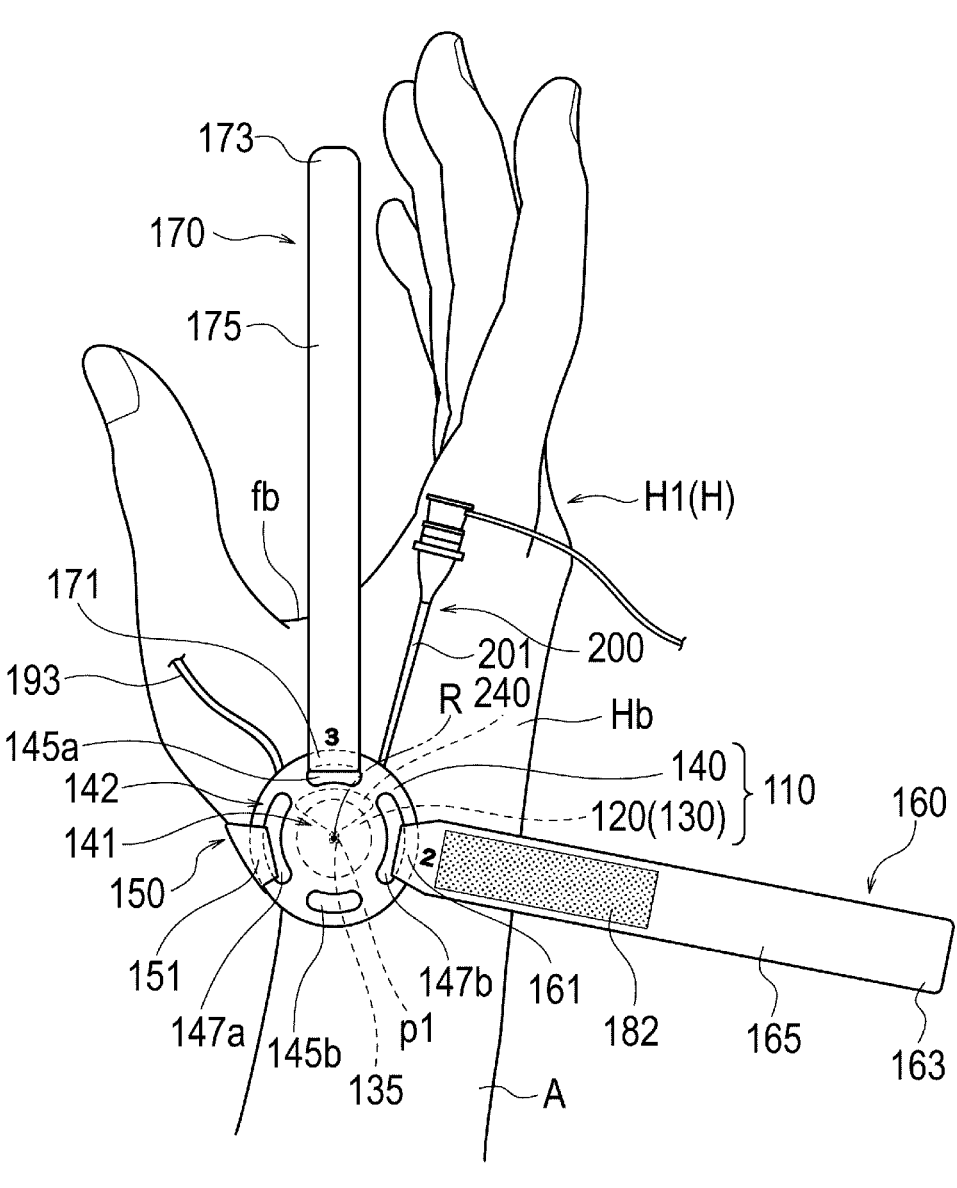
FIG. 22 is a view schematically showing a first usage example of the hemostatic device.
Figure 23:
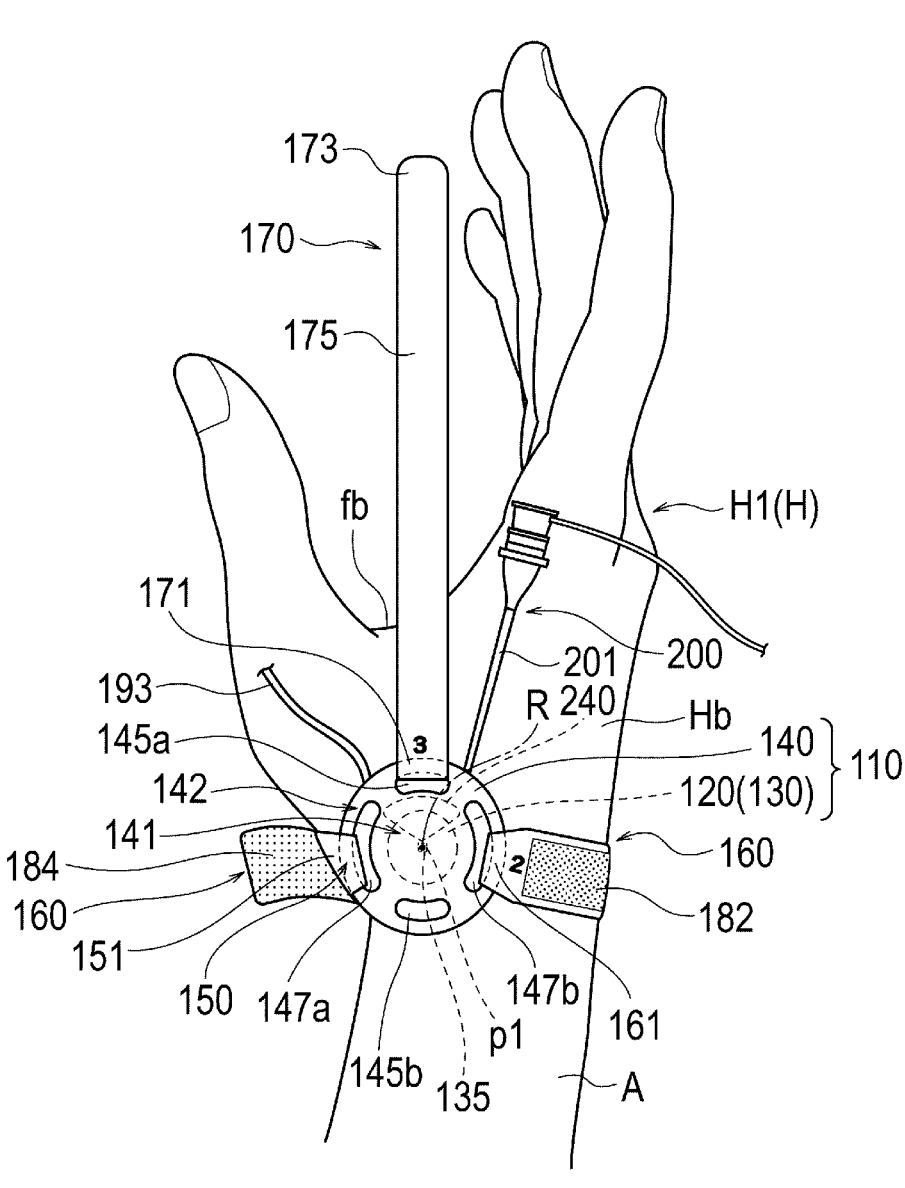
FIG. 23 is a view schematically showing the first usage example of the hemostatic device.

As shown in FIGS. 22 to 24, when the hemostatic device 100 is attached to the right hand H1 of the patient, the first band 150 and the second band 160 can be wrapped around an external periphery of the right hand H1.
Pressing Member As shown in FIGS. 5-7, the pressing member 110 includes the pressing portion 120 configured to compress the first puncture site p1 formed in the right hand H1 of the patient, and the support member 140 configured to fix the pressing portion 120.

Figure 6:
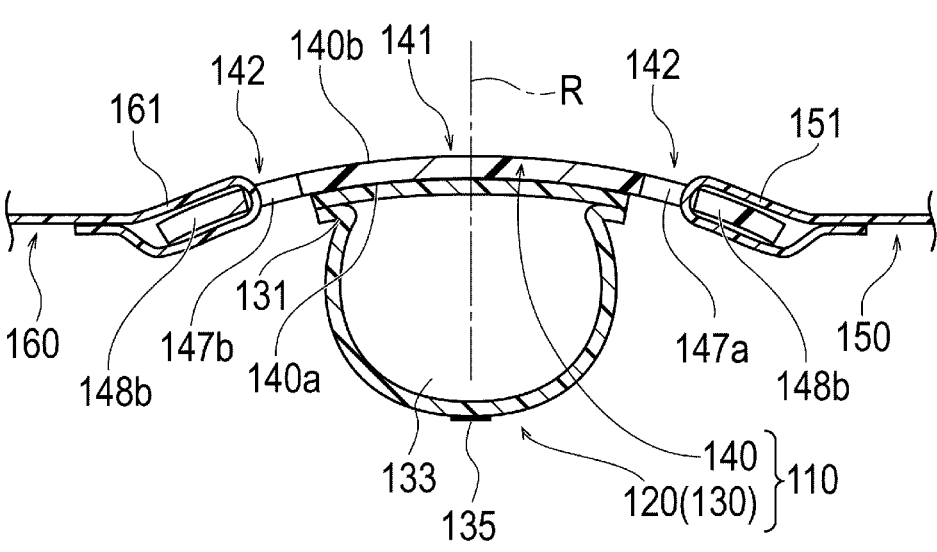
FIG. 6 is a cross-sectional view of a part in which a cross section of the hemostatic device along arrows VIA-VIA shown in FIG. 5 is vertically inverted, and shows a state where an inflatable member is inflated.
Figure 7:
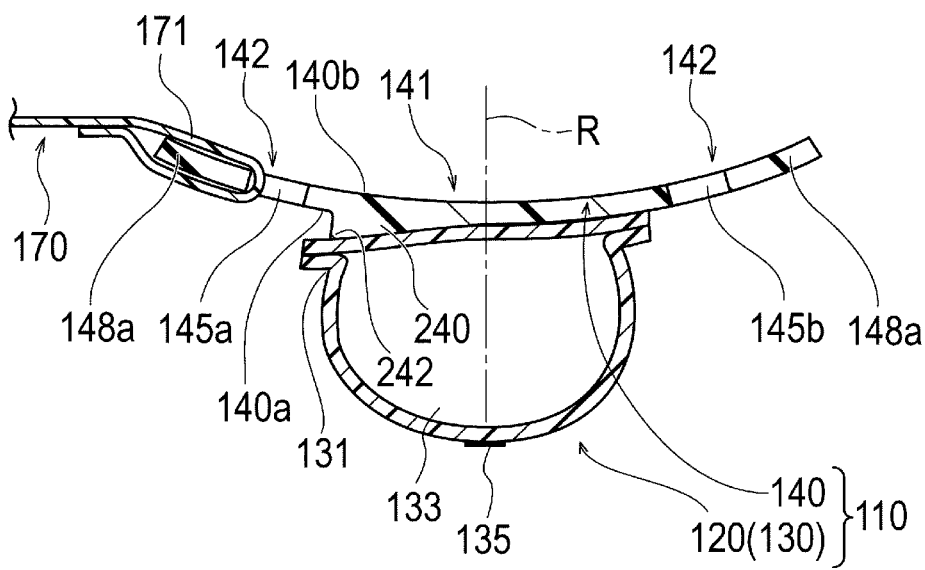
FIG. 7 is a cross-sectional view of a part in which a cross section of the hemostatic device along arrows VIIA-VIIA shown in FIG. 5 is vertically inverted, and shows a state where the inflatable member is inflated.

As shown in FIGS. 6 and 7, the pressing portion 120 can be implemented by, for example, an inflatable member 130 including a lumen 133 into which a fluid such as air can flow. FIGS. 6 and 7 are cross-sectional views of the inflatable member 130 in an inflated state. FIGS. 6 and 7 show cross-sectional views of a part in which cross sections taken along arrows 6A-6A and arrows 7A-7A shown in FIG. 5 are vertically inverted.

The inflatable member 130 can be implemented by, for example, a resin balloon. A tube 193 to be described later is connected to the lumen 133 of the inflatable member 130.

As shown in FIGS. 6, 7, 26, and 27, the inflatable member 130 is disposed on one surface 140*a* side of the support member 140. One surface 140*a* of the support member 140 is a surface on a surface side of the hand H of the patient when the hemostatic device 100 is attached to the hand H of the patient. The other surface 140*b* of the support member 140 is a surface opposite to the one surface 140*a*.

As shown in FIGS. 6 and 7, the inflatable member 130 can be connected to the one surface 140*a* of the support member 140. The inflatable member 130 and the support member 140 can be connected by, for example, fusion bonding or adhesion.

The inflatable member 130 has a circular shape in a plan view shown in FIGS. 1-5. A shape of the inflatable member 130 in the plan view is not limited to a circular shape. A cross-sectional shape of the inflatable member 130 before and after inflation, a constituent material for the inflation member 130, a specific structure of the inflation member 130, and the like are not particularly limited.

As shown in FIGS. 4, 5, 6, 7, 26, and 27, a marker 135 for aligning the inflatable member 130 with the first puncture site p1 is disposed on the inflatable member 130.

The marker 135 is disposed on an outer surface of a surface (surface on surface side of the hand H of the patient when hemostatic device 100 is attached to the hand H of the patient) of the inflatable member 130 opposite to a surface on a side on which the support member 140 is disposed.

A specific position for disposing the marker 135 is not particularly limited as long as the marker 135 is disposed on the inflatable member 130. The marker 135 may be disposed, for example, on an inner surface of the surface (surface on surface side of the hand H of the patient when hemostatic device 100 is attached to the hand H of the patient) of the inflatable member 130 opposite to the surface on the side on which the support member 140 is disposed.

As shown in FIG. 5, the marker 135 is disposed at a substantially central position of the inflatable member 130 in a plane direction. The marker 135 overlaps (i.e., extend over) a substantially central position of the support member 140 in the plane direction.

The marker 135 can be, for example, a rectangular marker in which the entire marker 135 is colored. A specific shape, a color, a formation method, a position, and the like of the marker 135 are not particularly limited. For example, the marker 135 may include a transparent central portion and a colored linear frame portion surrounding the central portion. For example, the marker 135 may be provided on the support member 140.

A specific configuration of the pressing portion 120 is not limited as long as the pressing portion 120 can apply a compressive force to the first puncture site p1 formed in the right hand H1 of the patient. The pressing portion 120 can also be implemented by, for example, a member made of a resin material such as plastic, gel, or the like, a member containing gel in which a water content is reduced with time to gradually reduce the compressive force, an elastic material such as a sponge-shaped substance, an aggregate of fibers such as cotton, a metal, a member having a predetermined three-dimensional shape (sphere, ellipsoid, triangular pyramid, or the like), or a combination of the member made of the resin material, the member made of gel, the member containing gel, the elastic material, and the aggregate of fibers as appropriate.

Support Member

As shown in FIGS. 3, 5, 6, and 7, the support member 140 includes the first region 141 in which the inflatable member 130 is disposed, and the second region 142 which is located outside the first region 141 and to which the third band 170, the first band 150, and the second band 160 are connectable.

The support member 140 has a circular shape in the plan view shown in FIG. 5.

The first region 141 is a region where the pressing portion 120 overlaps in the plan view shown in FIG. 5. The second region 142 is a region located outside the first region 141 in the plan view shown in FIG. 5.

The first region 141 can be freely defined based on an external shape and a size of the pressing portion 120 disposed on the support member 140. The second region 142 can be defined based on a relative positional relationship with the first region 141. Therefore, the first region 141 and the second region 142 can be appropriately changed according to the external shape and the size of the pressing portion 120 disposed on the support member 140.

As shown in FIGS. 5-8, the first region 141 is provided with the center point R that is the center of the first band 150 and the second band 160 when the first band 150 and the second band 160 slide. As shown in FIG. 8, the center point R is a center position when the first band 150 and the second band 160 slide along the second hole portions 147a and 147b. In the present embodiment, the center point R is located at a substantially central position of the support member 140 in the plane direction. Therefore, as shown in FIGS. 6-8, the center point R is located at a position overlapping the marker 135 when projected onto the inflatable member 130.

As shown in FIGS. 5, 6, 7, 9, and 10, a pair of first hole portions 145a and 145b facing each other with the pressing portion 120 interposed between the pair of first hole portions 145a and 145b, and the pair of second hole portions 147a and 147b facing each other with the pressing portion 120 interposed between the pair of second hole portions 147a and 147b at positions different from those of the pair of first hole portions 145a and 145b are formed in the second region 142.

In the description of the present specification, the first hole portion 145a is also referred to as "one first hole portion 145a". The first hole portion 145b is referred to as "the other first hole portion 145b". The second hole portion 147a is referred to as "one second hole portion 147a". The second hole portion 147b is referred to as "the other second hole portion 147b".

The one first hole portion 145a and the other first hole portion 145b are disposed on a distal side (fingertip side) of the hand H or a proximal side (forearm portion A side) of the hand H with the pressing portion 120 interposed between the one first hole portion 145a and the other first hole portion 145b as shown in FIG. 5. In the present embodiment, when the hemostatic device 100 is attached to the right hand H1 of the patient, the one first hole portion 145a is disposed on the distal side of the hand H relative to the pressing portion 120, and the other first hole portion 145b is disposed on the proximal side of the hand H relative to the pressing portion 120 (see FIG. 24).

When an attachment position of the hemostatic device 100 to the hand H of the patient is changed, the one first hole portion 145a and the other first hole portion 145b can be disposed by switching a positional relationship between the one first hole portion 145a and the other first hole portion 145b based on the pressing portion 120. That is, the one first hole portion 145a may be disposed on the proximal side of the hand H relative to the pressing portion 120, and the other first hole portion 145b may be disposed on the distal side of the hand H relative to the pressing portion 120.

Figure 3:
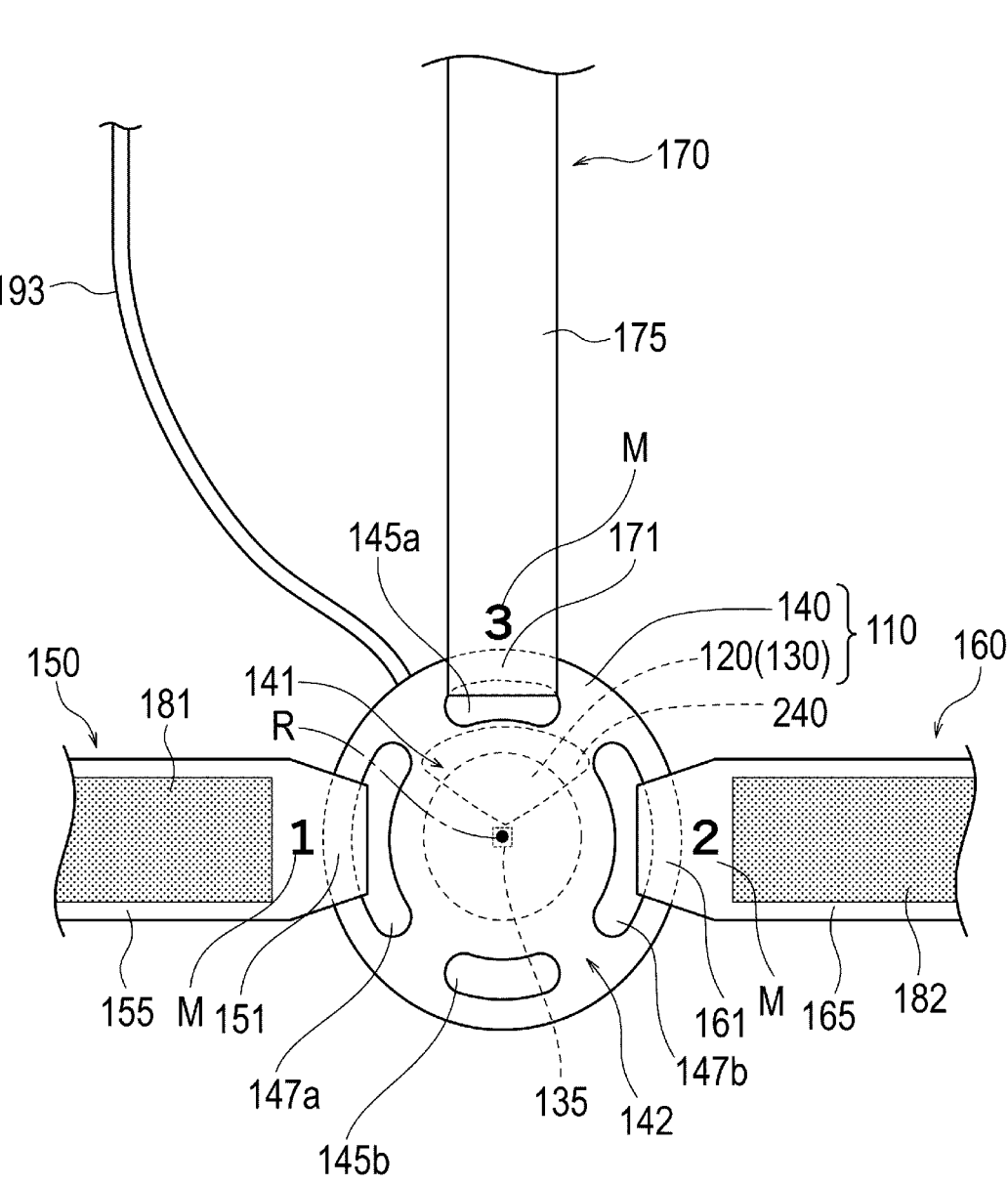
FIG. 3 is an enlarged plan view of a part of the hemostatic device viewed from the outer surface side of each band.
Figure 4:
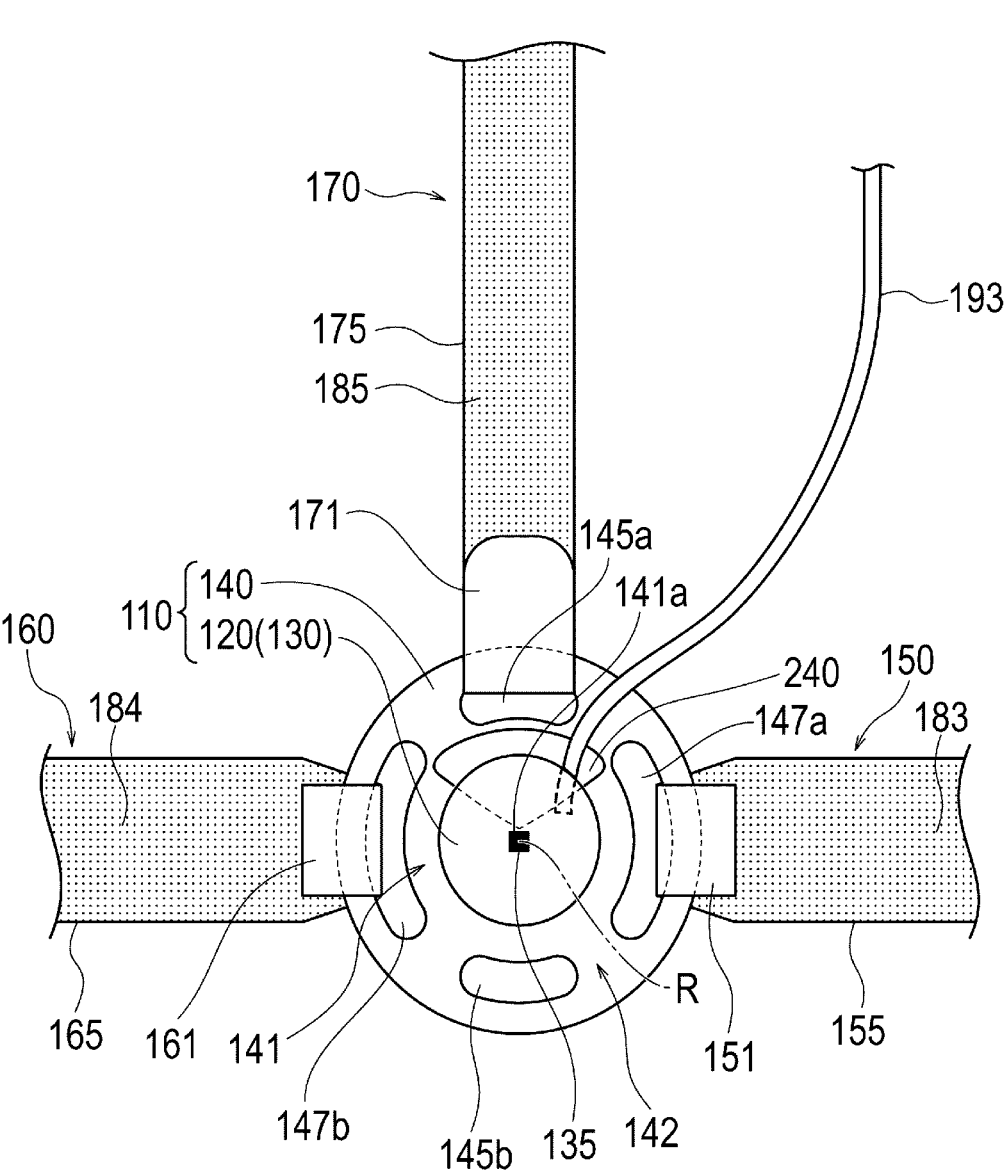
FIG. 4 is an enlarged plan view of a part of the hemostatic device viewed from the inner surface side of each band.

As shown in FIGS. 3-5, the one first hole portion 145a and the other first hole portion 145b are disposed on a virtual circle along an external shape of the support member 140. In the present embodiment, the support member 140 has a circular shape in the plan view shown in FIG. 5. Therefore, the one first hole portion 145a and the other first hole portion 145b are disposed along a circumferential direction of the second region 142 located outside the support member 140 relative to the first region 141.

The expression "disposed on a virtual circle" means that, assuming that a hole continuous in the circumferential direction of the second region 142 of the support member 140 is formed, the one first hole portion 145a and the other first hole portion 145b are disposed at any positions occupying a part of the hole with a gap between the one first hole portion 145a and the other first hole portion 145b. The similar applies to a positional relationship in which the one second hole portion 147a and the other second hole portion 147b to be described later are disposed on a virtual circle.

As shown in FIGS. 3, 4, 5, and 7, the third band 170 can be connected to the one first hole portion 145a.

In the present embodiment, a width (width in direction orthogonal to extending direction of third band 170) W3 of a third one end portion 171 of the third band 170 is substantially the same as a hole length L1 of the one first hole portion 145a (see FIG. 5). Therefore, the third band 170 is restricted from sliding around the center point R of the support member 140 in a state where the third band 170 is connected to the support member 140 via the one first hole portion 145a.

A hole length of each of the hole portions 145a, 145b, 147a, and 147b in the present specification means a linear distance between end portions of each of the hole portions 145a, 145b, 147a, and 147b located in the circumferential direction of the support member 140.

The width W3 of the third one end portion 171 of the third band 170 is substantially the same as a hole length L2 of the other first hole portion 145b (see FIG. 5). Therefore, the third band 170 can be restricted from sliding around the center point R of the support member 140 when the third band 170 is connected to the support member 140 via the other first hole portion 145b.

As shown in FIGS. 3-5, the one second hole portion 147a and the other second hole portion 147b are disposed with the pressing portion 120 interposed between the one second hole portion 147a and the other second hole portion 147b in a direction intersecting a straight line (virtual line C shown in FIG. 5) connecting the one first hole portion 145a and the other first hole portion 145b.

As shown in FIGS. 3 and 4, the one second hole portion 147a and the other second hole portion 147b are disposed on the virtual circle along the external shape of the support member 140.

As shown in FIG. 22, in the hemostatic device 100, when the one first hole portion 145a is disposed on the distal side of the right hand H1 of the patient relative to the pressing portion 120 and the other first hole portion 145b is disposed on the proximal side of the right hand H1 of the patient relative to the pressing portion 120, the one second hole portion 147a can be disposed on an inward side of the right hand H1 of the patient in the circumferential direction (side on which trunk (or torso) of patient is disposed) and the other second hole portion 147b can be disposed on an outward side of the right hand H1 of the patient in the circumferential direction.

A hole length L3 of the one second hole portion 147a is larger than the hole lengths L1 and L2 of the first hole portions 145a and 145b (see FIG. 5). Similarly, a hole length L4 of the other second hole portion 147b is larger than the hole lengths L1 and L2 of the first hole portions 145a and 145b. The hole length L3 of the one second hole portion 147a and the hole length L4 of the other second hole portion 147b are substantially the same length.

As shown in FIGS. 3, 4, 5, and 7, the first band 150 is connected to the one second hole portion 147a.

A width (width in direction orthogonal to extending direction of first band 150) W1 of a first one end portion 151 of the first band 150 is smaller than the hole length L3 of the one second hole portion 147a (see FIG. 5). Therefore, as shown in FIG. 8, in a state where the first band 150 is connected to the pressing member 110 via the one second hole portion 147a, the first band 150 can slide around the center point R of the support member 140 so as to change an angle in a radial shape within a range of a predetermined slide angle θ1.

The slide angle θ1 of the first band 150 can be freely defined by the width W1 of the first one end portion 151 of the first band 150 and the hole length L3 of the one second hole portion 147a. The slide angle θ1 of the first band 150 is not particularly limited, and can be set to be, for example, 1° to 75° about the center point R in the first region 141.

As shown in FIGS. 3, 4, 5, and 7, the second band 160 is connected to the other second hole portion 147b.

A width (width in direction orthogonal to extending direction of second band 160) W2 of a second one end portion 161 of the second band 160 is smaller than the hole length L4 of the other second hole portion 147b (see FIG. 5). Therefore, as shown in FIG. 8, in a state where the second band 160 is connected to the other second hole portion 147b, the second band 160 can slide about the center point R of the support member 140 so as to change an angle in a radial shape within a range of a predetermined slide angle θ2.

The slide angle θ2 of the second band 160 can be freely defined by the width W2 of the second one end portion 161 of the second band 160 and the hole length L4 of the other second hole portion 147b. The slide angle θ2 of the second band 160 is not particularly limited, and can be set to be, for example, 1° to 75° about the center point R in the first region 141.

As shown in FIG. 5, the first hole portions 145a and 145b and the second hole portions 147a and 147b can be disposed on virtual concentric circles centered on the center point R of the support member 140. The first hole portions 145a and 145b and the second hole portions 147a and 147b may not be disposed on virtual concentric circles.

The one first hole portion 145a and the other first hole portion 145b may have different shapes and hole lengths. The one second hole portion 147a and the other second hole portion 147b may have different shapes and hole lengths.

The hole length L1 of the one first hole portion 145a and/or the hole length L2 of the other first hole portion 145b may be larger than the width W3 of the third one end portion 171 of the third band 170. In such a configuration, the third band 170 can slide about the center point R of the support member 140 so as to change an angle in a radial shape in a state where the third band 170 is connected to the support member 140 via the one first hole portion 145a or the other first hole portion 145b.

As shown in FIGS. 7, 9, 10, and 27, a first curved region 148a that is curved in a convex shape away from the pressing portion 120 disposed on the one surface 140a of the support member 140 is formed in a portion where the pair of first hole portions 145a and 145b are disposed in the second region 142 of the support member 140.

Figure 27:
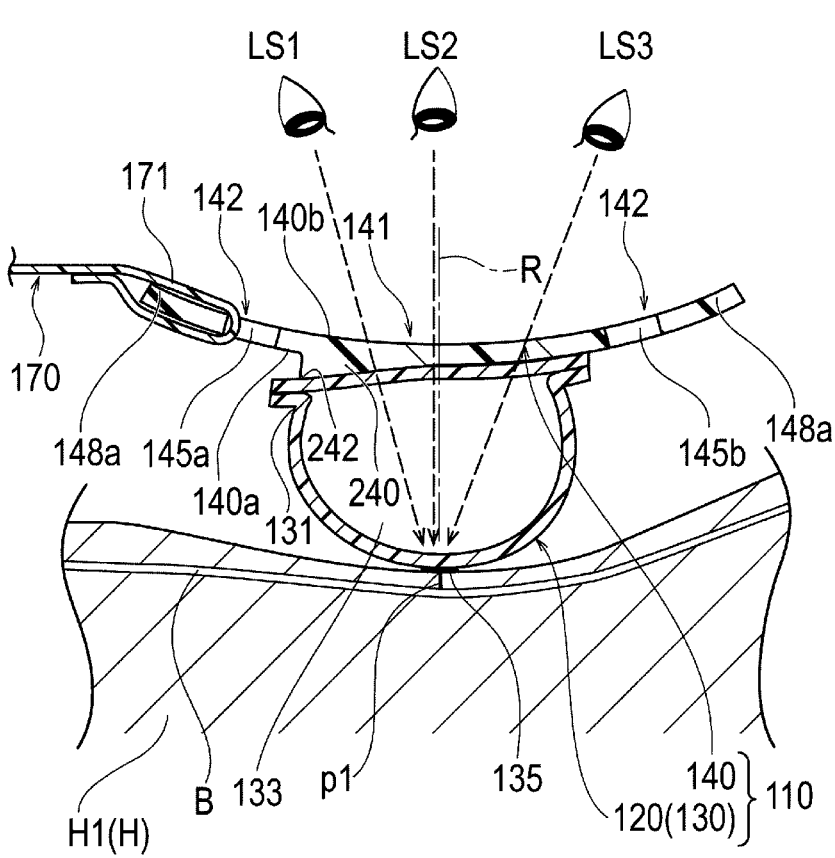
FIG. 27 is a cross-sectional view of a part taken along arrows XXVIIA-XXVIIA shown in FIG. 24.

As shown in FIG. 27, the "away from the pressing portion 120" is away from a surface of the hand H of the patient (upper side in FIG. 27) when the hemostatic device 100 is attached to the hand H of the patient.

As shown in FIGS. 6, 9, 10, and 26, a second curved region 148b that is curved in a convex shape to a pressing portion 120 side disposed on the one surface 140a of the support member 140 is formed in a portion where the pair of second hole portions 147a and 147b are disposed in the second region 142 of the support member 140.

Figure 26:
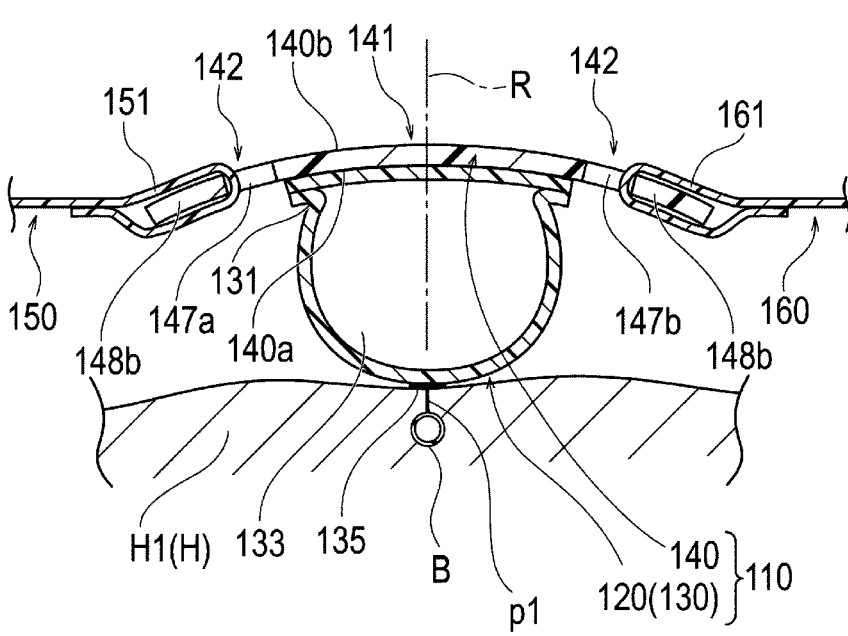
FIG. 26 is a cross-sectional view of a part taken along arrows XXVIA-XXVIA shown in FIG. 24.

As shown in FIG. 26, the "pressing portion 120 side" is a side close to the surface of the hand H of the patient (lower side in FIG. 26) when the hemostatic device 100 is attached to the hand H of the patient.

The support member 140 is preferably made of a material having a predetermined rigidity or hardness. When the support member 140 has a predetermined rigidity or hardness, as shown in FIGS. 26 and 27, the support member 140 can press the pressing portion 120 against the right hand H1 of the patient when the pressing portion 120 applies a compressive force to the first puncture site p1 formed in the right hand H1 of the patient. Accordingly, the pressing portion 120 can be prevented from being lifted up from the right hand H1 of the patient.

As a constituent material for the support member 140 having the hardness as described above, for example, an acrylic resin, polyvinyl chloride (particularly rigid polyvinyl chloride), polyolefin such as polyethylene, polypropylene, and polybutadiene, polystyrene, poly-(4-methylpentene-1), polycarbonate, an ABS resin, polymethyl methacrylate (PMMA), polyacetal, polyacrylate, polyacrylonitrile, poly-vinylidene fluoride, ionomer, acrylonitrile-butadiene-sty-rene copolymer, or polyethylene terephthalate (PET) can be used.

In the pressing portion 120 and the support member 140, portions overlapping each other in the plan view shown in FIGS. 4 and 5 can be transparent. When the pressing portion 120 and the support member 140 are configured as described above and the hemostatic device 100 is attached to the right hand H1 of the patient, as shown in FIGS. 22 and 23, an operator can visually check positions of the marker 135 and/or the first puncture site p1 through the pressing portion 120 and the support member 140 rather easily. The term "transparent" includes colored transparent, colorless trans-parent, and translucent.

Projection on Support Member

As shown in FIGS. 11A to 12B, the support member 140 includes a projection 240 protruding toward the pressing portion 120 on a third band 170 side of the first region 141. As shown in FIG. 12A, the projection 240 of the embodi-ment has a fan shape in the plan view when the support member 140 is viewed from the one surface 140a side on which the pressing portion 120 is disposed. In the plan view, an arc of the projection 240 extends close to an inner peripheral edge of the one first hole portion 145a. A central angle can be set to be an appropriate angle. A center of the fan shape is disposed at the substantially central position of the support member 140 in the plane direction.

As shown in FIG. 8, the first band 150 and the second band 160 are configured to slide about the center point R in the first region 141 of the support member 140. When the first band 150 and the second band 160 are wrapped around a wrist in a horizontal direction indicated by two-dot chain lines in FIG. 8, a center portion of the support member 140 can be firmly pressed. When the first band 150 and the second band 160 slide to positions indicated by solid lines in FIG. 8 and are obliquely wrapped around the wrist, a range pressed by the first band 150 and the second band 160 is shifted to a lower side of the support member 140 in the drawing (proximal side of hand H (forearm portion A side)). Depending on positions of the first band 150 and the second band 160 and a way in which the first band 150 and the second band 160 are wrapped around the wrist as described above, a force with which the first band 150 and the second band 160 press the support member 140 is not appropriately applied to a center of the support member 140, and the support member 140 may be inclined with a side of the support member 140 to which the third band 170 is con-nected (distal side (finger side)) lifted up. In such a case, a direction in which the puncture site p1 may be compressed by the pressing portion 120 is deviated, and the puncture site p1 may not be appropriately compressed. In such a state, the pressing portion 120 and the support member 140 can be firmly fixed to the hand of the patient by tightening the third band 170 disposed between fingers. However, it is necessary to tighten the third band 170, which may cause pain to the patient. Therefore, a mechanism capable of limiting the deviation of the pressing portion 120 in the compressing direction without depending on wrapping of the third band 170 may be required.

In relation to the fact that the first band 150 and the second band 160 are slidable about the center point R of the support member 140, a cause of the deviation of the pressing portion

120 in the compressing direction may be a physique of the patient (for example, size of hand) or a position of the puncture site (for example, puncture site is on distal side of snuff box of palmar artery) that affects the positions of the first band 150 and the second band 160 or a way in which the first band 150 and the second band 160 are wrapped around the wrist.

FIGS. 13A and 13B schematically show operations of the embodiment in which the support member 140 includes the projection 240. FIGS. 13C and 13D schematically show operations of a comparative example in which the support member 140 does not include the projection 240.

In the comparative example, as shown in FIG. 13C, when the support member 140 is not inclined, the compressing direction of the pressing portion 120 is directed toward the puncture site p1 (blood vessel puncture point). A compres-sive force of the pressing member 110 acts on the puncture site p1 in a vertical direction. As shown in FIG. 13D, when the support member 140 is inclined, the compressing direc-tion of the pressing portion 120 deviates rather greatly from a direction toward the puncture site p1 (amount of deviation=$\Delta 2$). Therefore, when the support member is inclined as shown in FIG. 13D depending on the physique of the patient or the position of the puncture site, the hemostatic device cannot effectively apply a compressive force to the puncture site p1.

In the case of the embodiment, the support member 140 includes the projection 240 protruding toward the pressing portion 120 on the third band 170 side of the first region 141. Therefore, as shown in FIG. 13A, when the support member 140 is not inclined, the compressing direction of the pressing portion 120 is slightly deviated from the direction toward the puncture site p1. However, as shown in FIG. 13B, when the support member 140 is inclined, the compressing direction of the pressing portion 120 is directed to the direction toward the puncture site p1 with a limited amount of deviation from the direction toward the puncture site p1 (amount of deviation=$\Delta 1$ ($\Delta 1 < \Delta 2$)) compared with the comparative example. Therefore, in the hemostatic device, even when the support member 140 is inclined depending on the physique of the patient or the position of the puncture site, a change in the compressing direction of the pressing portion 120 is relatively small, and thus it is possible to effectively apply the compressive force to the puncture site p1.

Figures 12A, 12B:
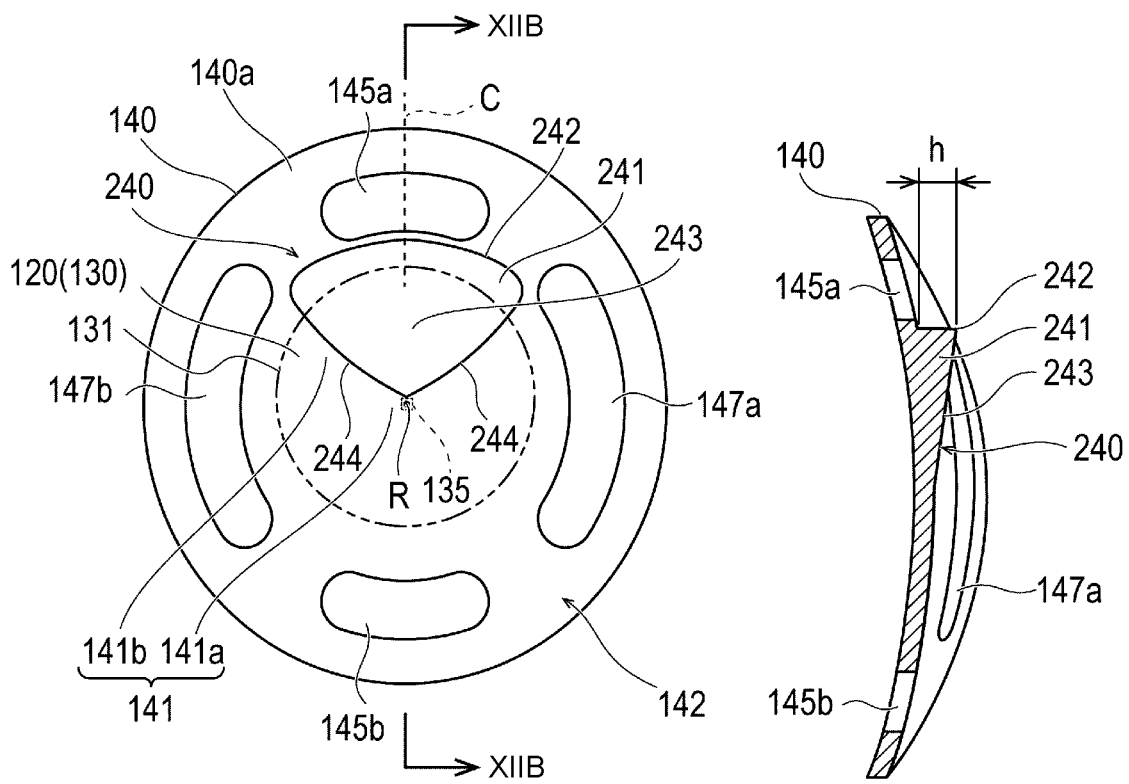
FIG. 12A is a plan view of the support member viewed from the one surface side on which the pressing portion is disposed.
FIG. 12B is a cross-sectional view taken along a line XIIB-XIIB in FIG. 12A.

As shown in FIGS. 12A and 12B, the projection 240 extends from the third band 170 side of the first region 141 to a center point R side of the first region 141. A thickness of the projection 240 decreases from the third band 170 side of the first region 141 to the center point R side of the first region 141.

Due to the projection 240 having such a shape, when the support member 140 is inclined, the compressing direction of the pressing portion 120 is directed to the direction toward the puncture site p1 with an effectively limited amount of deviation from the direction toward the puncture site p1.

The first region 141 of the support member 140 includes a central region 141a located at a center of the first region 141, and a curved region 141b curved in a direction away from the pressing portion 120 from the central region 141a toward a peripheral edge of the support member 140. The projection 240 is located in the curved region 141b, and at least a part of the projection 240 protrudes to the pressing portion 120 side relative to the central region 141a (see FIG. 12B).

As shown in FIGS. 9-11C, the support member 140 is curved in a convex shape from the second curved region 148b (second curved region 148b located on left and right in FIG. 10) disposed on the one surface 140a of the support member 140 to the pressing portion 120 side. The central region 141a is a region of the support member 140 where an apex of the convex shape is located. Therefore, the central region 141a has a radius of curvature larger than that of the second curved region 148b and has a planar shape.

The "direction away from the pressing portion 120" is a direction away from the surface of the hand H of the patient (upward in FIG. 27) when the hemostatic device 100 is attached to the hand H of the patient as shown in FIG. 27.

The projection 240 is located in the curved region 141b, and at least a part of the projection 240 protrudes to the pressing portion 120 side relative to the central region 141a. Therefore, the projection 240 can apply a compressive force in an oblique direction to a central region 141a side to the pressing portion in a state where the hemostatic device is attached to the hand of the patient and the pressing portion is inflated. In addition, since the projection 240 protrudes to the pressing portion 120 side relative to the central region 141a, the projection 240 can reliably come into contact with the pressing portion and apply a compressive force to the pressing portion without depending on a connection method between the pressing portion and the support member. Therefore, even when the support member 140 is inclined, the compressing direction of the pressing portion is directed to a direction toward the puncture site p1 with a limited amount of deviation from the direction toward the puncture site p1 by the projection of the support member. A dimension (reference sign h in FIG. 12B) of the projection 240 protruding to the pressing portion 120 side relative to the central region 141a is not particularly limited, but can be, for example, about 3 mm.

The projection 240 has an inclined portion 241 that extends from the third band 170 side of the first region 141 toward the central region 141a located at the center of the first region 141 and comes into contact with the pressing portion 120.

The expression "central region 141a located at the center of the first region 141" does not only include a surface that extends to a certain extent. A "point" can also be regarded as a surface as long as a dimension actually exists. Therefore, the "central region 141a" should be interpreted as including the "point".

Since the inclined portion 241 of the projection 240 defines a slope from the third band 170 side of the first region 141 toward the central region 141a located at the center of the first region 141, the slope comes into contact with the pressing portion 120 and stably presses the pressing portion 120. Therefore, even when the support member 140 is inclined, the compressing direction of the pressing portion is more reliably directed to the direction toward the puncture site p1 with a limited amount of deviation from the direction toward the puncture site p1 by the projection of the support member.

A direction in which the inclined portion 241 extends from the third band 170 side of the first region 141 toward the central region 141a located at the center of the first region 141 is a direction from an upper side to a lower side in FIG. 12A. A cross section of the inclined portion 241 in an extending direction (cross section shown in FIG. 12B) may be a planar surface, a concave curved surface, or a convex curved surface.

The pressing member 110 has the marker 135 for aligning the pressing portion 120 with the puncture site p1, and a center of the marker 135 is located at a position not overlapping the projection 240.

The "position where the center of the marker 135 does not overlap the projection 240" means that a projection image of the center of the marker 135 does not overlap the projection 240 when the marker 135 is projected onto the support member 140 along a direction orthogonal to the support member 140. When the pressing portion 120 is the inflatable member 130, the "position where the center of the marker 135 does not overlap the projection 240" means that a projection image of the center of the marker 135 does not overlap the projection 240 when the marker 135 is projected onto the support member 140 along the direction orthogonal to the support member 140 during deflation of the inflatable member 130. The center of the marker 135 is a portion located in a middle of an external shape of the marker 135 in the plan view. For example, when the marker 135 is a square or a rectangle, the center of the marker 135 is a center of gravity of the square or the rectangle. When the marker 135 is a circle, the center of the marker 135 is a middle point of a diameter of the circle. When the marker 135 is an ellipse, the center of the marker 135 is an intersection of a major axis and a minor axis of the ellipse.

Since the center of the marker 135 is disposed at a position not overlapping the projection 240, when the operator uses the marker 135 to dispose the pressing portion 120 at the puncture site p1, the pressing portion 120 can be suitably disposed at the puncture site p1 along a surface of the hand. Therefore, when the hemostatic device 100 is attached to the patient, it is possible to improve a fit feeling of the hemostatic device 100 to the surface of the hand of the patient. Since the center of the marker 135 is located at a position not overlapping the projection 240, it is possible to ensure visibility of the operator when the operator uses the marker 135 to dispose the pressing portion 120 at the puncture site p1.

Figure 11A:
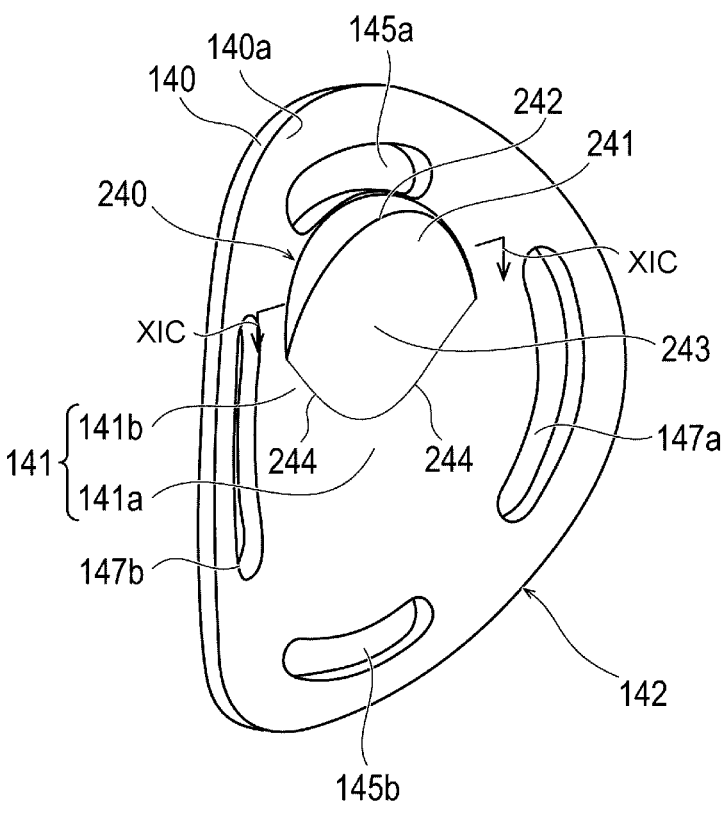
FIG. 11A is a perspective view of the support member viewed from one surface side on which a pressing portion is disposed.

As shown in FIGS. 11A, 12A, and 12B, the projection 240 has the inclined portion 241 that extends from the third band 170 side of the first region 141 to the central region 141a side located at the center of the first region 141 and comes into contact with the pressing portion 120. The inclined portion 241 has a slope on an inner surface 243 of the projection 240 from the third band 170 side of the first region 141 toward the central region 141a located at the center of the first region 141. In addition, a part of the slope is located at a position overlapping the external shape of the marker 135. Note that a distal end of the slope does not overlap the center of the marker 135. Here, the expression "a part of the slope is located at a position overlapping the external shape of the marker 135. Note that a distal end of the slope does not overlap the center of the marker 135" means that when the marker 135 is projected onto the support member 140 along the direction orthogonal to the support member 140, a part of the projection image of an external edge of the marker 135 overlaps the slope of the projection 240, and a projection image of the center of the marker 135 does not overlap the distal end of the slope of the projection 240. Note that when the pressing portion 120 is the inflatable member 130, the expression "a part of the slope is located at a position overlapping the external shape of the marker 135. Note that a distal end of the slope does not overlap the center of the marker 135" means that, during deflation of the inflatable member 130, when the marker 135 is projected onto the support member 140 along the direction orthogonal to the support member 140, a part of the projection image of the external edge of the marker 135 overlaps the slope of the projection 240, and the projection image of the center of the marker 135 does not overlap the distal end of the slope of the projection 240.

Since the inclined portion 241 of the projection 240 has the slope inclined from the third band 170 side of the first region 141 to the central region 141*a* side of the first region 141, the distal end of the slope of the projection 240 can be smoothly connected to a surface of the support member 140. Therefore, when the operator uses the marker 135 to dispose the pressing portion 120 at the puncture site p1, the pressing portion 120 can be disposed at the puncture site p1 along the surface of the hand. Therefore, when the hemostatic device 100 is attached to the patient, the hemostatic device 100 can be fitted to the surface of the hand of the patient. Since the support member 140 is located at a position where a part of the slope of the projection 240 overlaps the external shape of the marker 135, the support member 140 can reliably press the pressing portion 120 to a center side of the marker 135 where the puncture site p1 is located.

As shown in FIGS. 11A and 12A, the slope of the projection 240 has a fan shape centered on the distal end of the slope in the plan view.

Since the projection 240 has a fan shape centered on the distal end of the slope, a region where the marker 135 and the projection 240 overlap can be reduced in a direction intersecting a direction in which the third band 170 extends. Therefore, when the hemostatic device 100 is attached to the patient, the hemostatic device 100 can be fitted to the surface of the hand of the patient while the support member 140 reliably presses the pressing portion 120 to the center side of the marker 135 located at the puncture site p1.

Figure 25:
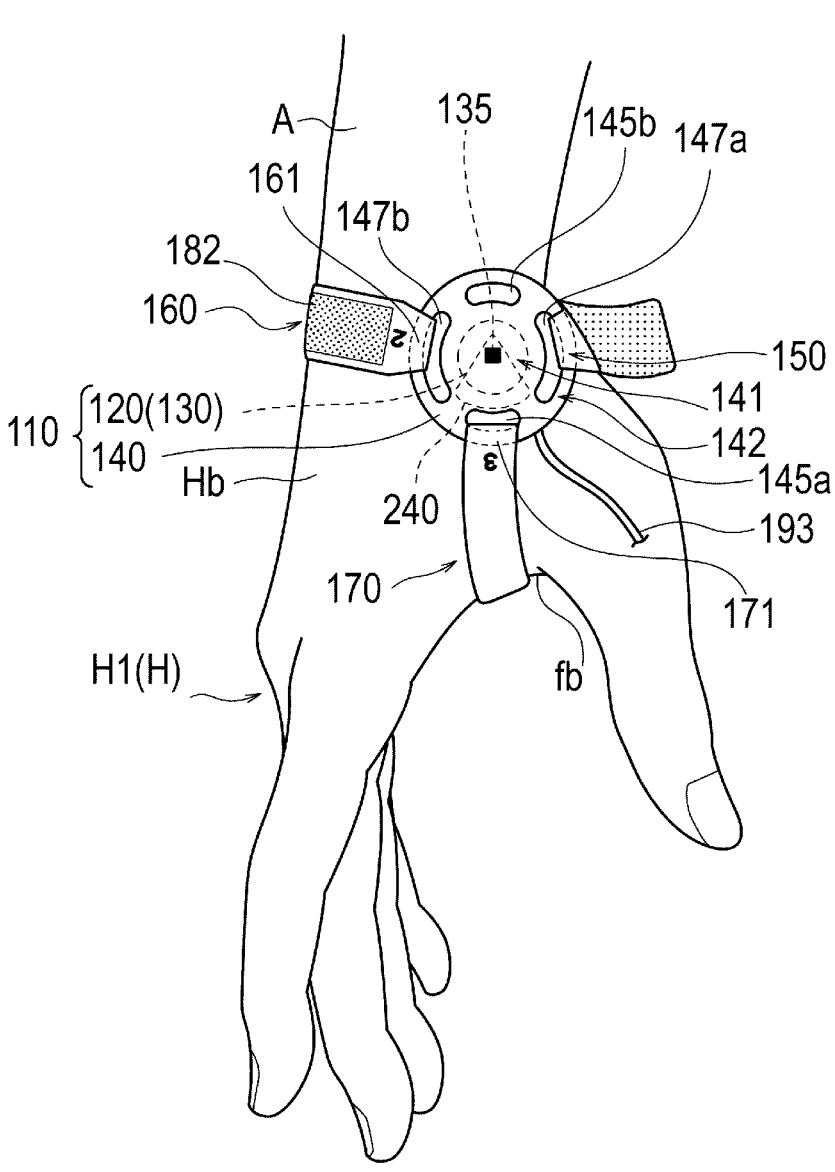
FIG. 25 is a view schematically showing the first usage example of the hemostatic device.

As shown in FIGS. 6 and 7, the pressing portion 120 can be implemented by the inflatable member 130 that can be inflated by injecting a fluid. The thickness of the projection 240 of the support member 140 is larger than a thickness of the central region 141*a* of the support member 140. That is, a thickness from an outer surface of the support member 140 to the slope of the projection 240 is larger than the thickness of the central region 141*a* of the support member 140. Therefore, as shown in FIGS. 25 and 27 to be described later, the projection 240 can be implemented as a lens that magnifies the marker 135 when the marker 135 is viewed through the projection 240 in a state where the inflatable member 130 is inflated.

As shown in FIG. 27, a line of sight of a person who views the marker 135 includes a line of sight LS1 for viewing the marker 135 obliquely through the projection 240 from the distal side (finger side), a line of sight LS2 for viewing the marker 135 substantially straight through a substantially central portion of the support member 140, and a line of sight LS3 for viewing the marker 135 obliquely through the support member 140 from the proximal side (forearm portion A side) of the hand H. The person who views the marker 135 includes the operator or the patient. A line of sight of the operator is usually the line of sight LS1, and a line of sight of the patient is usually the line of sight LS2 or the line of sight LS3. The projection 240 of the support member 140 has a shape with a thickness different from that of other portions of the support member 140. Therefore, for example, when the operator views the marker 135 obliquely through the projection 240 from the distal side (finger side) along the line of sight LS1, the projection 240 serves as a magnifying glass for magnifying the marker 135 (see FIG. 25). Accordingly, the operator can view the marker 135 in a magnified manner, and can rather easily check a puncture point. The projection 240 not only magnifies the marker 135 but also magnifies a vicinity of the puncture point. Therefore, the marker 135 and the puncture point can be rather easily aligned with each other, and a hemostatic state can be rather easily observed. For example, when the patient views the marker 135 along the line of sight LS2 or the line of sight LS3, the marker 135 is not seen in a magnified manner (see FIG. 24). Thus, by selecting a direction in which the marker 135 is viewed, it is possible to select whether the marker 135 is magnified.

Figure 11B:
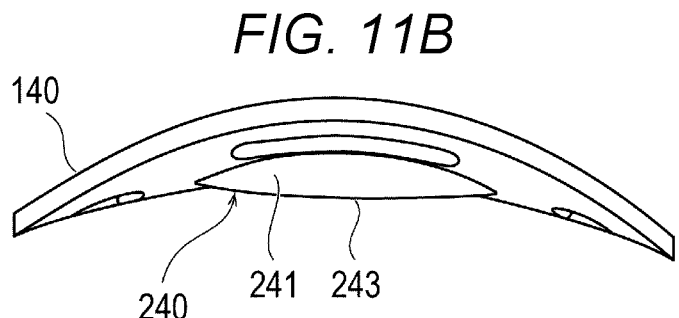
FIG. 11B is a view of the support member viewed from a distal side (finger side) to which a third band is connected.

The projection 240 of the embodiment extends from the third band 170 side of the first region 141 to the center point R side of the first region 141. Further, as shown in FIG. 11, the thickness of the projection 240 decreases from the third band 170 side of the first region 141 to the center point R side of the first region 141. In this case, when the operator views the marker 135 obliquely through the projection 240 from the distal side (finger side) along the line of sight LS1, the projection 240 has a shape like a lens with a convex shape on one side, and thus the marker 135 can be reliably magnified and viewed.

As shown in FIGS. 5 and 12A, the projection 240 has an external shape that is bilaterally symmetrical with respect to a major axis C of the third band 170.

The thickness of the projection 240 protruding toward the pressing portion 120 is bilaterally symmetrical with respect to the major axis C of the third band 170. Therefore, regardless of whether the hemostatic device 100 is attached to the right hand H1 or a left hand of the patient, even when the support member 140 is inclined, the compressing direction of the pressing portion 120 is directed to the direction toward the puncture site p1 with a limited amount of deviation from the direction toward the puncture site p1. As shown in FIG. 5, the major axis C of the third band 170 extends along the extending direction of the third band 170 and passes through a center of the third band 170 in a width direction.

As shown in FIGS. 6 and 7, the pressing portion 120 can be implemented by the inflatable member 130 that can be inflated by injecting a fluid. As shown in FIGS. 7 and 12A, the inflatable member 130 has a peripheral edge portion 131 located at a peripheral edge of a portion that can be inflated by injecting a fluid. Note that the peripheral edge portion 131 does not mean a fusion margin, and is a term that refers to an exterior periphery of an inflatable portion. As shown in FIG. 7, a peripheral edge 242 (thickest portion) of the projection 240 has a shape matching (overlapping) the peripheral edge portion 131 of the inflatable member 130.

As shown in FIG. 12A, the peripheral edge 242 of the projection 240 has an arc shape, and the peripheral edge portion 131 of the inflatable member 130 has a circular shape. Since the peripheral edge 242 of the projection 240 extends along the peripheral edge portion 131 of the inflatable member 130, one side (upper side in FIG. 12A) of the peripheral edge portion 131 of the inflatable member 130 can be effectively pressed. Accordingly, when the support member 140 is inclined, the compressing direction of the pressing portion 120 is directed to the direction toward the puncture site p1 with a relatively limited amount of deviation from the direction toward the puncture site p1. From a viewpoint of effectively pressing one side of the peripheral edge portion 131 of the inflatable member 130, the peripheral edge 242 of the projection 240 is located at a position overlapping the peripheral edge portion 131 of the inflatable member 130, or is located on the third band 170 side relative to the peripheral edge portion 131 of the inflatable member 130 in the plan view. That is, as shown in FIG. 12, the pressing member 110 is preferably configured such that the projection 240 covers a part of the peripheral edge portion 131 of the inflatable member 130 on the third band 170 side of the support member 140 in the plan view.

As shown in FIGS. 11A-12B, the projection 240 has the inner surface 243 located in a direction of facing the pressing portion 120. As shown in FIG. 11C, a cross section of the inner surface 243 of the projection 240 in a direction intersecting the direction in which the third band 170 extends is a plane.

The "direction in which the third band 170 extends" is an upper-lower direction in FIG. 12A.

The inner surface 243 of the projection 240 has a planar cross section in the direction intersecting the direction in which the third band 170 extends. Therefore, the inner surface 243 of the projection 240 is in surface contact with the pressing portion 120 and stably presses the pressing portion 120. Therefore, even when the support member 140 is inclined, the compressing direction of the pressing portion 120 is reliably directed to the direction toward the puncture site p1 with a limited amount of deviation from the direction toward the puncture site p1 by the projection 240 of the support member 140.

The projection 240 has an end portion 244 that constitutes a distal end of the projection 240 in an extending direction from the peripheral edge 242 of the projection 240 located on the third band 170 side to the center point R side of the first region 141. The end portion 244 of the projection 240 is continuous with the first region 141 of the support member 140. The end portion 244 of the projection 240 is a portion having a radius of the fan shape in FIG. 12A. As shown in FIG. 12B, the end portion 244 of the projection 240 is smoothly continuous with the first region 141 of the support member 140. Therefore, no step occurs at a boundary between the end portion 244 of the projection 240 and the first region 141 of the support member 140. Accordingly, in the support member 140, since no step occurs at the boundary portion between the end portion 244 of the projection 240 and the first region 141, it is possible to reduce a decrease in visibility due to a step in the inner surface of the support member 140. Since the support member 140 is configured such that the end portion 244 of the projection 240 and the first region 141 are smoothly continuous with each other, an extra space due to the step is not generated between the inflatable member 130 and the inner surface of the support member 140. Therefore, when the inflatable member 130 is fixed to the support member 140 during manufacturing, it is possible to prevent a gap from occurring between the inflatable member 130 and the inner surface of the support member 140. Accordingly, in the hemostatic device 100, when the inflatable member 130 such as a balloon is depressurized, it is possible to prevent an unexpected behavior of the inflatable member 130 due to a part of the inflatable member 130 entering the step.

Band

As shown in FIGS. 1 to 4, the third band 170 includes a third main portion 175, the third one end portion 171 configured to be connected to the one first hole portion 145a of the support member 140, and a free third other end portion 173.

Note that the "free other end portion" in the present specification means that there is no direct or articulated connection relationship with other members in a state where the hemostatic device 100 is not attached (state where hemostatic device is not attached to patient).

Figure 2:
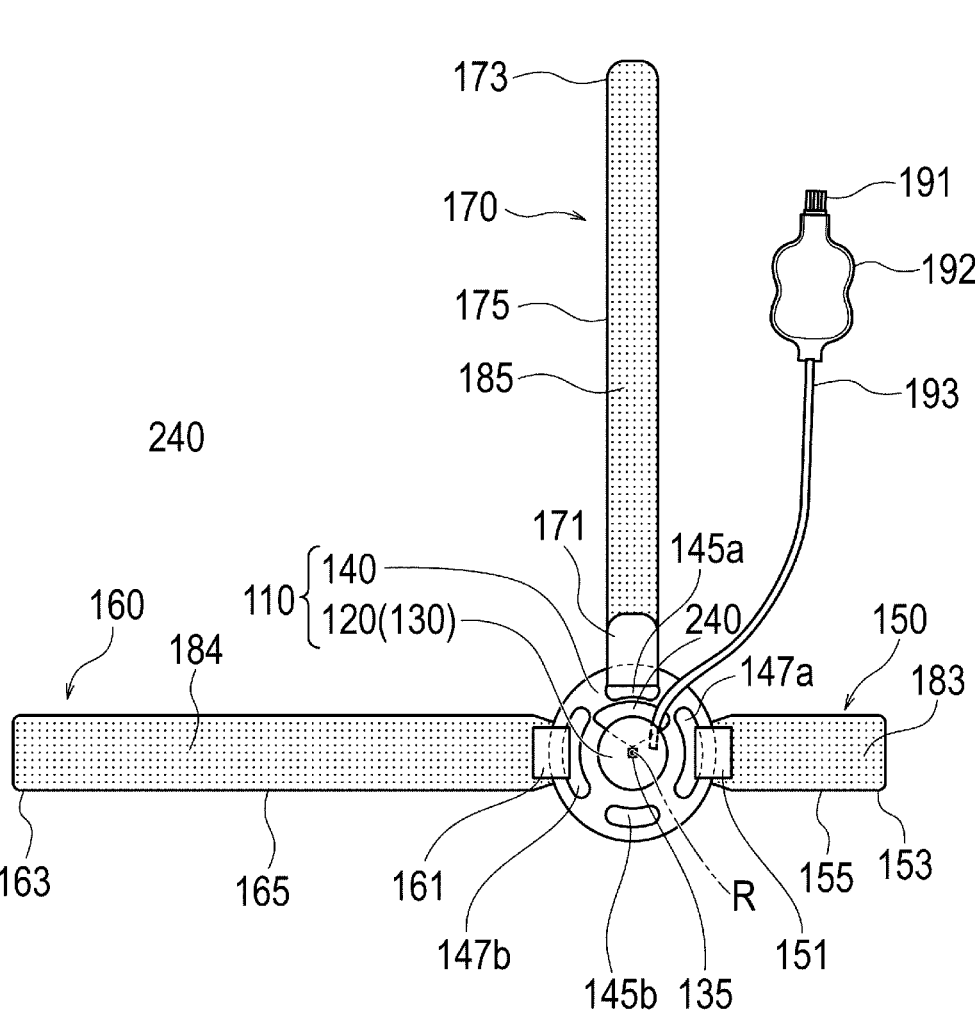
FIG. 2 is a plan view showing the hemostatic device according to the embodiment, viewed from an inner surface side of each band.

As shown in FIGS. 1 and 2, the third main portion 175 extends along a longitudinal direction of the third band 170.

As shown in FIG. 7, the third one end portion 171 of the third band 170 can be inserted into and wrapped around the one first hole portion 145a of the support member 140. The third band 170 is connected to the support member 140 via the third one end portion 171 and the one first hole portion 145a.

As described above, in the present embodiment, the width W3 of the third one end portion 171 of the third band 170 is substantially the same as the hole length L1 of the one first hole portion 145a (see FIG. 5). Therefore, the third band 170 is restricted from sliding about the center point R of the support member 140 in a state where the third band 170 is connected to the support member 140.

A structure for connecting the third one end portion 171 of the third band 170 and the support member 140 is not particularly limited. For example, a fixing member (for example, hook-and-loop fastener) capable of holding and releasing a state of being wrapped around the one first hole portion 145a can be disposed on the third one end portion 171 of the third band 170. When the third band 170 is configured as described above, the third band 170 can be connected to and disconnected from the support member 140.

As shown in FIGS. 1-4, the first band 150 includes a first main portion 155, the first one end portion 151 configured to be connected to the one second hole portion 147a of the support member 140, and a free first other end portion 153.

As shown in FIGS. 1 and 2, the first main portion 155 extends along a longitudinal direction of the first band 150.

As shown in FIG. 6, the first one end portion 151 of the first band 150 can be inserted into and wrapped around the one second hole portion 147a of the support member 140. The first band 150 is connected to the support member 140 via the first one end portion 151 and the one second hole portion 147a.

As described above, the width W1 of the first one end portion 151 of the first band 150 is smaller than the hole length L3 of the one second hole portion 147a (see FIG. 5). Therefore, the first band 150 is slidable about the center point R of the support member 140 in a state where the first band 150 is connected to the support member 140 (see FIG. 8).

A structure for connecting the first one end portion 151 of the first band 150 and the support member 140 is not particularly limited. For example, a fixing member (for example, hook-and-loop fastener) capable of holding and releasing a state of being wrapped around the one second hole portion 147a can be disposed on the first one end portion 151 of the first band 150. When the first band 150 is configured as described above, the first band 150 can be connected to and disconnected from the support member 140.

As shown in FIGS. 1-4, the second band 160 includes a second main portion 165, the second one end portion 161 configured to be connected to the other second hole portion 147b of the support member 140, and a free second other end portion 163.

As shown in FIGS. 1 and 2, the second main portion 165 extends along a longitudinal direction of the second band 160.

As shown in FIG. 6, the second one end portion 161 of the second band 160 can be inserted into and wrapped around the other second hole portion 147b of the support member 140. The second band 160 is connected to the support member 140 via the second one end portion 161 and the other second hole portion 147b.

As described above, the width W2 of the second one end portion 161 of the second band 160 is smaller than the hole length L4 of the other second hole portion 147b (see FIG. 5). Therefore, the second band 160 is slidable about the center point R of the support member 140 in a state where the second band 160 is connected to the support member 140 (see FIG. 8).

A structure for connecting the second one end portion 161 of the second band 160 and the support member 140 is not particularly limited. For example, a fixing member (for example, hook-and-loop fastener) capable of holding and releasing a state of being wrapped around the other second hole portion 147*b* can be disposed on the second one end portion 161 of the second band 160. When the second band 160 is configured as described above, the second band 160 can be connected to and disconnected from the support member 140.

A symbol M (including figures and characters) for identifying the bands 150, 160, and 170 are provided on one end portions 151, 161, and 171 sides of the bands 150, 160, and 170. In the present embodiment, a number "1" is provided on the one end portion 151 side of the first band 150, a number "2" is provided on the one end portion 161 side of the second band 160, and a number "3" is provided on the one end portion 171 side of the third band 170. The numbers provided at the bands 150, 160, and 170 correspond to an order of wrapping the bands 150, 160, and 170 when the operator attaches the hemostatic device 100 to the "right hand H1 of the patient. Therefore, the operator can attach the bands 150, 160, and 170 on the right hand H1 of the patient in a correct order by viewing the symbol M. Note that a size, a color, a formation method, a position, and the like of the symbol M are not particularly limited. For example, the method of forming the symbol M can also be formed by making a hole in a band other than printing. When the symbol M is formed by making a hole, it is desirable, for example, that a periphery of the hole be of a single color at least. A reason for the periphery of the hole to be of a single color is that it can be difficult to see the symbol when the hole is made in multiple colors. Certainly, the entire band may be of a single color.

A constituent material for the bands 150, 160, and 170 is not particularly limited, and can be, for example, a vinyl chloride resin, a polyamide resin, a polyamide elastomer resin, a polyurethane resin, or a polyester resin. A shape, a length, and a thickness of each of the bands 150, 160, and 170 are not particularly limited.

Fixing Member

As shown in FIGS. 1-4, the hemostatic device 100 includes four fixing members which are a first fixing member 181, a second fixing member 182, a fourth fixing member 184, and a fifth fixing member 185.

As shown in FIGS. 1 and 3, the first fixing member 181 is disposed on an outer surface of the first band 150. The second fixing member 182 is disposed on an outer surface of the second band 160.

As shown in FIGS. 2 and 4, a third fixing member 183 is disposed on an inner surface of the first band 150. The fourth fixing member 184 is disposed on an inner surface of the second band 160. The fifth fixing member 185 is disposed on an inner surface of the third band 170. The third fixing member 183 for the first band 150 is used to fix the first band 150 to the support member 140. The third fixing member 183 of the first band 150 is not used to wrap the first band 150 around the wrist.

The inner surface of each of the bands 150, 160, and 170 is a surface at the surface side of the patient when the hemostatic device 100 is attached to the patient, and the outer surface of each of the bands 150, 160, and 170 is a surface on a side opposite to the inner surface.

The first fixing member 181 and the second fixing member 182 can be implemented by male sides of the hook-and-loop fasteners. The third fixing member 183, the fourth fixing member 184, and the fifth fixing member 185 can be implemented by female sides of the hook-and-loop fasteners. The hook-and-loop fastener in the present specification is a fastener that can be attached to and detached from the surface, and is, for example, Magic Tape® or Velcro®.

Note that specific structures of the fixing members 181, 182, 183, 184, and 185 are not limited as long as the pressing portion 120 can be fixed to the right hand H1 by connecting the bands 150, 160, and 170 to each other in a state where the hemostatic device 100 is disposed on the right hand H1 of the patient. For example, omission of some of the fixing members, and changes in positions of the fixing members in the bands 150, 160, and 170 can be freely performed. When each of the fixing members 181, 182, 183, 184, and 185 is implemented by a hook-and-loop fastener, the male and female sides of the hook-and-loop fastener may be interchanged. Each of the fixing members 181, 182, 184, and 185 may be, for example, a snap, a button, a clip, or a frame member in which a hole portion is formed.

Injection Portion

As shown in FIGS. 1 and 2, the hemostatic device 100 includes an injection portion 191 for injecting a fluid into the inflatable member 130.

The injection portion 191 can include a connector having a built-in check valve. A syringe, for example, can be connected to the injection portion 191.

A cushioning member 192 having an inflatable space is disposed between the injection portion 191 and the inflatable member 130. The cushioning member 192 is implemented by a flexible bag-shaped member having a space defined in the flexible bag-shaped member. The cushioning member 192 may be provided with an arrow-shaped marker indicating an insertion direction of the syringe into the injection portion 191.

The injection portion 191 is connected to one end of the cushioning member 192. A lumen of the injection portion 191 communicates with the space in the cushioning member 192. While the check valve built in the injection portion 191 is closed, communication between the lumen of the injection portion 191 and the space of the cushioning member 192 is cut off.

A flexible tube 193 is connected to the other end of the cushioning member 192. A lumen of the tube 193 communicates with the space of the member 192. The tube 193 is connected to the inflatable member 130 at the other end portion opposite to one end portion connected to the cushioning member 192. The lumen of the tube 193 communicates with the lumen 133 of the inflatable member 130.

When inflating the inflatable member 130, the operator inserts a front tube portion of the syringe into the injection portion 191 and opens the check valve. The operator injects air in the syringe into the lumen 133 of the inflatable member 130 by pushing a plunger of the syringe in a state where the check valve of the injection portion 191 is opened.

When the air is injected into the lumen 133 of the inflatable member 130, the inflatable member 130 is inflated. When the inflatable member 130 is inflated, the cushioning member 192 communicating with the lumen 133 of the inflatable member 130 via the tube 193 inflates. The operator can rather easily recognize that the inflatable member 130 is inflated without leakage of air by visually checking inflation of the cushioning member 192.

When deflating the inflatable member 130, the operator inserts the front tube portion of the syringe into the injection portion 191 and pulls the plunger of the syringe. By performing the above operation, the operator can discharge the air in the lumen 133 of the inflatable member 130 to the syringe.

Usage Example of Hemostatic Device

Next, a first usage example of the hemostatic device 100 will be described with reference to FIGS. 22-27.

In the first usage example, a procedure of using the hemostatic device 100 when stopping bleeding of the first puncture site p1 formed in the right hand H1 of the patient will be described.

FIG. 22 shows a state where the sheath tube of the introducer 200 was inserted into the first puncture site p1 and various procedures were performed.

As shown in FIG. 22, the operator disposes the pressing member 110 on the dorsal Hb side of the right hand H1 of the patient. At this time, the operator can appropriately position the pressing member 110 at the first puncture site p1 by disposing the marker 135 at the first puncture site p1 while visually checking the position of the marker 135 disposed on the inflatable member 130.

The operator may pull out a part of the sheath tube of the introducer 200 from the first puncture site p1 formed in the right hand H1 of the patient after finishing the procedure using the introducer 200 and before attaching the hemostatic device 100 to the right hand H1 of the patient. For example, the operator can start an attachment operation for the hemostatic device 100 after pulling out the sheath tube by about 2 cm to 3 cm to a hand-side of the operator in a state where the sheath tube of the introducer 200 is indwelt in the blood vessel B.

As shown in FIGS. 22 and 23, the operator wraps the first band 150 and the second band 160 along the external periphery of the right hand H1 of the patient. The operator can fix the first band 150 and the second band 160 via the first fixing member 181 (see FIG. 1) disposed on the outer surface of the first band 150 and the fourth fixing member 184 (see FIG. 2) disposed on the inner surface of the second band 160 by bringing the fourth fixing member 184 into contact with the first fixing member 181.

When wrapping the first band 150 and the second band 160 along the external periphery of the right hand H1 of the patient, the operator can slide the first band 150 or slide the second band 160 about the center point R of the first region 141 of the support member 140. By sliding the first band 150 and the second band 160 around the pressing portion 120, the operator can adjust angles and positions at which the bands 150 and 160 are wrapped around the right hand H1 of the patient. For example, the operator can slide the bands 150 and 160 about the center point R of the support member 140 so as to change the angles in a radial manner within the ranges of the slide angles θ1 and θ2 (see FIG. 8) so that the bands 150 and 160 are wrapped around the right hand H1 of the patient at a position on the forearm portion A side (proximal side) relative to the first puncture site p1.

As shown in FIG. 24, the operator inserts the third band 170 through the interdigital portion fb located between the thumb and the forefinger of the right hand H1 of the patient, and disposes a part of the third band 170 on a palm side of the right hand H1 of the patient. At this time, the operator can fix the third band 170 and the second band 160 via the second fixing member 182 (see FIG. 1) disposed on the outer surface of the second band 160 and the fifth fixing member 185 (see FIG. 2) disposed on the inner surface of the third band 170 by bringing the fifth fixing member 185 into contact with the second fixing member 182.

As described above, the operator can rather effectively prevent the hemostatic device 100 from being deviated from the right hand H1 of the patient by disposing the first band 150 and the second band 160 so as to be wrapped around the external periphery of the right hand H1 of the patient and further disposing a part of the third band 170 so as to be hooked on the interdigital portion fb between the thumb and the forefinger of the right hand H1 of the patient.

The operator inflates the inflatable member 130 by injecting air into the inflatable member 130 in a state where the syringe is connected to the injection portion 191. In the hemostatic device 100, as shown in FIGS. 26 and 27, when the inflatable member 130 is inflated, the inflatable member 130 applies a compressive force to the first puncture site p1 of the right hand H1 of the patient.

As shown in FIGS. 24 and 27, when attaching the hemostatic device 100 to the hand H of the operator, the operator can dispose the first curved region 148a formed near the one first hole portion 145a at a position on the distal side of the right hand H1 of the patient. The operator can dispose the first curved region 148a formed near the other first hole portion 145b at a position on the proximal side of the right hand H1 of the patient. By disposing the hemostatic device 100 in this manner, when the patient moves the right hand H1 in the upper-lower direction or a left-right direction by twisting the wrist in a state where the hemostatic device 100 is attached to the right hand H1 of the patient, the first curved region 148a help prevent a peripheral edge portion of the support member 140 from being attached to the right hand H1 of the patient. Similarly, in the hemostatic device 100, when the patient moves the right hand H1 as described above, the first curved region 148a formed near the other first hole portion 145b helps prevent the peripheral edge portion of the support member 140 from being attached to the right hand H1 of the patient. Accordingly, the hemostatic device 100 can prevent the patient from feeling uncomfortable or pain due to the peripheral edge portion of the support member 140 being attached to or biting into the right hand H1 of the patient while stop bleeding of the first puncture site p1 formed in the right hand H1 of the patient.

As shown in FIGS. 24 and 26, when the hemostatic device 100 is attached to the hand H of the patient, the operator can fix the pressing portion 120 to the right hand H1 of the patient such that the second curved region 148b formed in the support member 140 is disposed along a part of the external periphery of the right hand H1 of the patient. When the pressing portion 120 is inflated in a state where the hemostatic device 100 is attached to the right hand H1 of the patient, the second curved region 148b of the support member 140 presses the pressing portion 120 along a part of the external periphery of the right hand H1 of the patient. Accordingly, the hemostatic device 100 can help prevent the pressing portion 120 from being lifted up from the right hand H1 of the patient. Therefore, the hemostatic device 100 can rather effectively apply a compressive force to the first puncture site p1 by the inflatable member 130.

After inflating the inflatable member 130, the operator removes the sheath tube of the introducer 200 from the first puncture site p1 formed in the right hand H1 of the patient as shown in FIG. 24. While using the hemostatic device 100 to stop bleeding, the operator confirms that there is no bleeding from the first puncture site p1 formed in the right hand H1 of the patient. When there is bleeding from the first puncture site p1 formed in the right hand H1 of the patient, the operator adjusts an injection amount of air into the inflatable member 130.

According to the above procedure, the operator can stop bleeding of the first puncture site p1 formed in the right hand H1 of the patient using the hemostatic device 100.

According to the hemostatic device 100, it is possible to select whether the marker 135 is magnified by selecting a direction in which the marker 135 is viewed. FIG. 24 shows a state where the marker 135 is viewed along the line of sight LS2 or the line of sight LS3 shown in FIG. 27. FIG. 25 shows a state where the marker 135 is viewed along the line of sight LS1 shown in FIG. 27. As shown in FIGS. 24 and 27, for example, when the patient views the marker 135 along the line of sight LS2 or the line of sight LS3, the marker 135 is not seen In a magnified manner. On the other hand, as shown in FIGS. 25 and 27, for example, when the operator views the marker 135 obliquely through the projection 240 from the distal side (finger side) along the line of sight LS1, the projection 240 serves as a magnifying glass for magnifying the marker 135. Accordingly, the operator can view the marker 135 in a magnified manner, and can rather easily check the puncture point.

FIG. 28 shows a second usage example of the hemostatic device 100. The second usage example is a usage example of the hemostatic device 100 when stopping bleeding of the second puncture site p2 formed in the right hand H1 of the patient.

As shown in FIG. 28, the operator attaches the hemostatic device 100 to the right hand H1 of the patient when stopping bleeding of the second puncture site p2 formed in the right hand H1 of the patient. The second puncture site p2 formed in the right hand H1 of the patient is located on the distal side of the right hand H1 of the patient relative to the above first puncture site p1 (see FIG. 21). When wrapping the bands 150 and 160 around the right hand H1 of the patient, the operator slides the bands 150 and 160 about the center point R of the first region 141 of the support member 140. For example, the operator slides the bands 150 and 160 so that the bands 150 and 160 are wrapped around the right hand H1 of the patient at a position closer to the forearm portion A side (proximal side) than the first puncture site p1. The operator can help prevent a portion on the distal side of the right hand H1 of the patient from being restrained by the bands 150 and 160 by wrapping the bands 150 and 160 around positions on the proximal side of the right hand H1 of the patient.

Although not shown, the hemostatic device 100 can also be used when stopping bleeding of a puncture site formed in the left hand of the patient. The puncture site formed in the left hand is, for example, a puncture site formed in an artery located in a snuff box of a palmar artery running on a dorsal side of the left hand of the patient, and a puncture site formed in a distal radial artery located on a distal side of the snuff box of the palmar artery running on the dorsal side of the left hand of the patient. The latter puncture site is located on a distal side of the left hand relative to the former puncture site with reference to the extensor pollicis longus muscle tendon located on the dorsal side of the left hand of the patient.

When stopping bleeding of the puncture site in the left hand, the hemostatic device 100 can be attached to the left hand of the patient in a similar procedure as in the first usage example and in the second usage example. The operator can adjust the angle and position at which the bands 150 and 160 are wrapped around the left hand by sliding the bands 150 and 160 about the center point R of the first region 141 of the support member 140 according to a position of each puncture site in the left hand of the patient. By adjusting the angle and position at which the bands 150 and 160 are wrapped around the left hand, the operator can help prevent a portion on the distal side of the left hand of the patient from being restrained by the bands 150 and 160 when stopping bleeding of the puncture site.

As described through the usage examples, the hemostatic device 100 can be attached to both the right hand H1 and the left hand of the patient. The hemostatic device 100 can be attached to the hand H of the patient so that a portion on the distal side of the hand H of the patient is not restrained by the bands 150 and 160 when the hemostatic device 100 is used for stopping bleeding of the puncture sites p1 and p2 formed at different positions in the right hand H1 of the patient and when the hemostatic device 100 is used for stopping bleeding of puncture sites formed at different positions in the left hand of the patient.

As described above, the hemostatic device 100 according to the present embodiment includes: the pressing member 110 configured to compress the puncture site p1 formed in the patient; the first band 150 configured to be connected to the pressing member 110; the second band 160 configured to be connected to the pressing member 110; and the third band 170 configured to be connected to the pressing member 110. The pressing member 110 includes the pressing portion 120 configured to compress the puncture site p1 and the support member 140 configured to fix the pressing portion 120. The support member 140 has the first region 141 in which the pressing portion 120 is located, and the second region 142 which is located outside the first region 141 and to which the first band 150, the second band 160, and the third band 170 are connectable. The first band 150 and the second band 160 have the center point R that is the center in the first region 141 when the first band 150 and the second band 160 slide in a state of being connected to the second region 142, and slide around the pressing portion 120 in the second region 142 about the center point R. The third band 170 extends in a different direction from the first band 150 and the second band 160 in a state where the third band 170 is connected to the second region 142, and is configured to be disposed between fingers of the patient. The support member 140 includes the projection 240 protruding toward the pressing portion 120 on the third band 170 side of the first region 141.

According to the hemostatic device 100 configured as described above, the first band 150 and the second band 160 can slide about the center point R located in the first region 141 of the support member 140 in a state where the first band 150 and the second band 160 are connected to the second region 142. Therefore, the hemostatic device can adjust angles and positions of the two bands 150 and 160 relative to the hand of the patient by sliding the two bands around the pressing portion 120 with the pressing portion 120 as the center while disposing the pressing member 110 at the puncture site p1 formed in the hand of the patient. By adjusting the angles and positions of the first band 150 and the second band 160, the operator can suitably attach the hemostatic device 100 to the patient in accordance with the physique and the puncture position of the patient while disposing the pressing member 110 at the puncture site p1 formed in the hand of the patient. When both the first band 150 and the second band 160 are located on a wrist side, the side of the support member 140 to which the third band 170 is connected may lift up. Since the hemostatic device 100 includes the projection 240 protruding toward the pressing portion 120 on the third band 170 side of the first region 141 of the support member 140, the compressing direction of the pressing portion 120 is directed to the direction toward the puncture site p1 with a limited amount of deviation from the direction toward the puncture site p1. Accordingly, the hemostatic device 100 can be suitably attached to the patient in accordance with the physique and the puncture position p1 of the patient, and the compressive force can be effectively applied to the puncture site p1.

The projection 240 may extend from the third band 170 side of the first region 141 to the center point R side of the first region 141. The thickness of the projection 240 may be decreased from the third band 170 side of the first region 141 to the center point R side of the first region 141.

According to the hemostatic device 100 configured as described above, the thickness of the projection 240 decreases from the third band 170 side of the first region 141 to the center point R side of the first region 141. Therefore, even when both the first band 150 and the second band 160 are located on the wrist side and the side of the support member 140 to which the third band 170 is connected is lifted up in a state where the hemostatic device 100 is attached to the hand of the patient, the support member 140 can apply, to the pressing portion 120, a compressive force in an oblique direction to the center point R side of the first region 141 from the third band 170 side of the first region 141 of the support member 140 that is likely to lift up from the surface of the hand. Therefore, even when the support member 140 is inclined, the compressing direction of the pressing portion 120 is directed to the direction toward the puncture site p1 with a limited amount of deviation from the direction toward the puncture site p1 by the projection 240.

The first region 141 of the support member 140 may include the central region 141*a* located at the center of the first region 141, and the curved region 141*b* curved in the direction away from the pressing portion 120 from the central region 141*a* toward the peripheral edge 242 of the support member 140. The projection 240 may be located in the curved region 141*b*, and at least a part of the projection 240 may protrude to the pressing portion 120 side relative to the central region 141*a*.

According to the hemostatic device 100 configured as described above, at least a part of the projection 240 protrudes to the pressing portion 120 side relative to the central region 141*a* of the support member 140. Therefore, the projection 240 can reliably come into contact with the pressing portion 120 on the third band 170 side of the first region 141 of the support member 140, which is likely to lift up from the surface of the hand, and can apply a compressive force to the pressing portion 120. Since the projection 240 is located on a peripheral edge 242 side of the support member 140 on the support member 140, a compressive force to the central region 141*a* side can be applied to the pressing portion 120. Therefore, even when the support member 140 is inclined, the compressing direction of the pressing portion 120 is directed to the direction toward the puncture site p1 with a limited amount of deviation from the direction toward the puncture site p1 by the projection 240 of the support member 140.

The projection 240 may have an inclined portion 241 that extends from the third band 170 side of the first region 141 toward the central region 141*a* located at the center of the first region 141 and comes into contact with the pressing portion 120.

According to the hemostatic device 100 configured as described above, the projection 240 has the inclined portion 241 extending from the third band 170 side of the first region 141 toward the central region 141*a* of the first region 141. Therefore, the inclined portion 241 of the projection 240 is in surface contact with the pressing portion 120 and stably presses the pressing portion 120. Therefore, even when the support member 140 is inclined, the compressing direction of the pressing portion 120 is more reliably directed to the direction toward the puncture site p1 with a limited amount of deviation from the direction toward the puncture site p1 by the projection 240 of the support member 140.

The pressing member 110 may have the marker 135 that aligns the pressing portion 120 with the puncture site p1, and the center of the marker 135 may be located at a position not overlapping the projection 240.

According to the hemostatic device 100 configured as described above, since the center of the marker 135 is located at a position not overlapping the projection 240, when the operator uses the marker 135 to dispose the pressing portion 120 at the puncture site p1, the pressing portion 120 can be suitably disposed at the puncture site p1 along the surface of the hand. Therefore, when the operator attaches the hemostatic device 100 to the patient, it is possible to improve a fit feeling to the surface of the hand of the patient. In the hemostatic device 100, since the center of the marker 135 is located at the position not overlapping the projection 240, it is possible to help ensure visibility of the operator when the operator uses the marker 135 to dispose the pressing portion 120 at the puncture site p1.

The pressing portion 120 may be implemented by the inflatable member 130 that is configured to be inflated by injecting a fluid. The thickness of the projection 240 may be larger than the thickness of the central region 141*a* located at the center of the first region 141 of the support member 140.

According to the hemostatic device 100 configured as described above, the pressing portion 120 is implemented by the inflatable member 130, and the thickness of the projection 240 is larger than the thickness of the central region 141*a* of the support member 140. That is, the thickness from the outer surface of the support member 140 to the slope of the projection 240 is larger than the thickness of the central region 141*a* of the support member 140. Therefore, the projection 240 is implemented as a lens for magnifying the marker 135 when the marker 135 is viewed through the projection 240 in a state where the inflatable member 130 is inflated. When a person who views the marker 135 views the marker 135 obliquely through the projection 240 from the distal side (finger side), the projection 240 serves as a magnifying glass for magnifying the marker 135. Accordingly, a person who views the marker 135 can view the marker 135 in a magnified manner, and can rather easily check the puncture point. The projection 240 not only magnifies the marker 135 but also magnifies the vicinity of the puncture point. Therefore, the marker 135 and the puncture point can be rather easily aligned with each other, and the hemostatic state can be rather easily observed. When a person who views the marker 135 views the marker 135 without passing through the projection 240, the marker 135 is not viewed in a magnified manner. Thus, by selecting a direction in which the marker 135 is viewed, it is possible to select whether the marker 135 is magnified.

The projection 240 may have an external shape that is bilaterally symmetrical with respect to the major axis of the third band 170.

According to the hemostatic device 100 having the projection 240 having the above shape, the thickness of the projection 240 protruding toward the pressing portion 120 is bilaterally symmetrical with respect to the major axis C of the third band 170. Therefore, regardless of whether the support member 140 is disposed to the right hand H1 or the left hand of the patient, even when the support member 140 is inclined, the compressing direction of the pressing portion 120 is directed to the direction toward the puncture site p1 with a limited amount of deviation from the direction toward the puncture site p1.

The pressing portion 120 may be implemented by the inflatable member 130 having the peripheral edge portion 131 located at the peripheral edge of the portion that is configured to be inflated by injecting a fluid, and the peripheral edge 242 of the projection 240 may have a shape matching the peripheral edge portion 131 of the inflatable member 130.

According to the hemostatic device 100 having the projection 240 having the above shape, since the peripheral edge 242 of the projection 240 extends along the peripheral edge portion 131 of the inflatable member 130, the one side (upper side in FIG. 12A) of the peripheral edge portion 131 of the inflatable member 130 can be effectively pressed. Accordingly, when the support member 140 is inclined, the compressing direction is directed to the direction toward the puncture site p1 with a limited amount of deviation from the direction toward the puncture site p1. In the hemostatic device 100, since the peripheral edge 242 of the projection 240 extends along the peripheral edge portion 131 of the inflatable member 130, it is possible to reduce a thickness of the hemostatic device 100 (thickness from support member 140 to inflatable member 130) while ensuring a maximum region where the inflatable member 130 is disposed on the projection 240. Therefore, the inflatable member 130 can be pressed by the projection 240 while preventing an external shape of the hemostatic device 100 from becoming bulky.

Modifications of Projection of Support Member

FIGS. 14A to 20B show various modifications of the projection 240 of the support member 140.

Figures 14A, 14B, 15A, 15B:
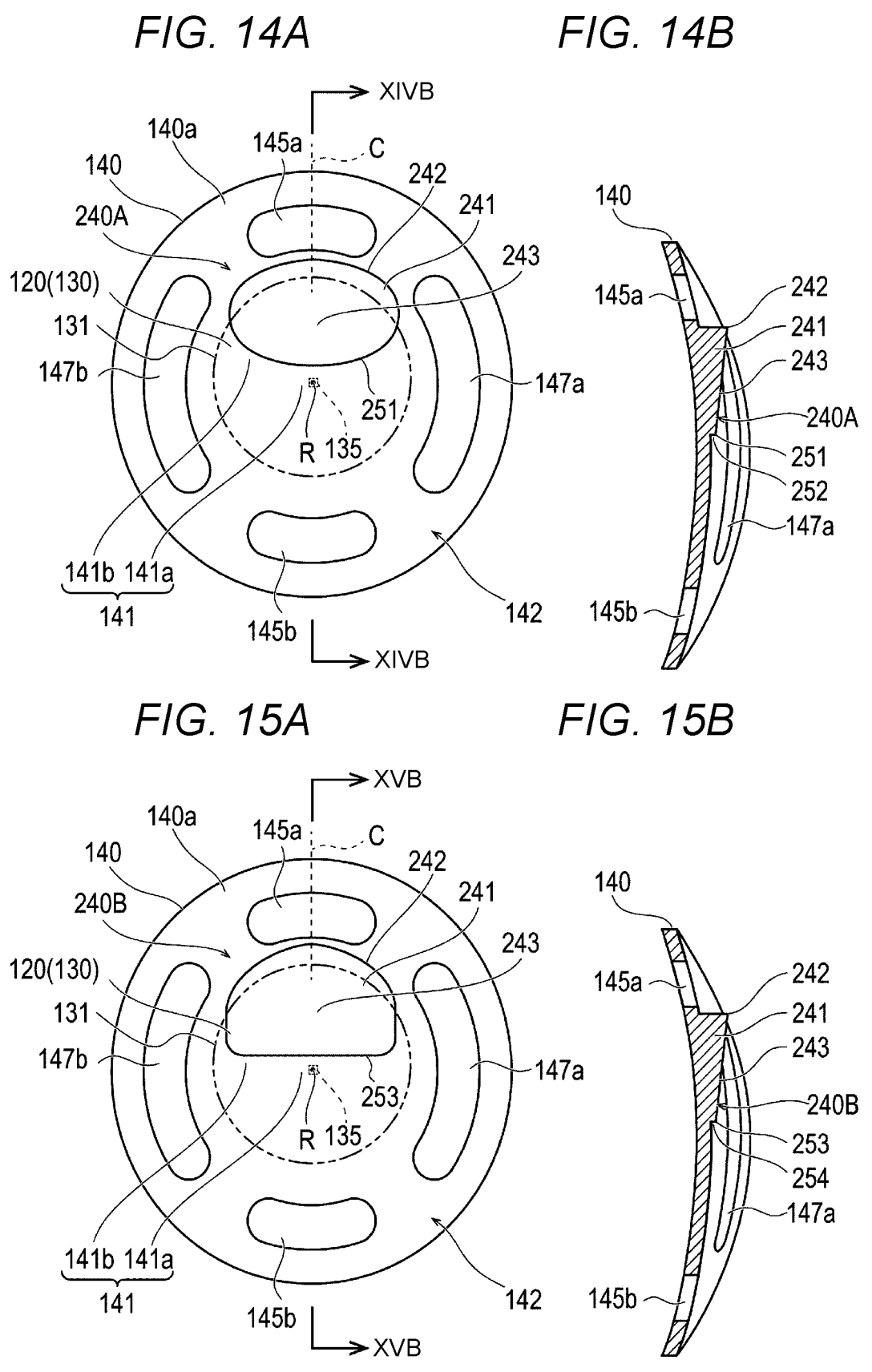

As shown in FIG. 14A, a projection 240A of a first modification has an elliptical shape in the plan view when the support member 140 is viewed from the one surface 140a side on which the pressing portion 120 is disposed. In the plan view, an arc of the projection 240A extends close to the inner peripheral edge of the one first hole portion 145a. The projection 240A is disposed on an upper side in the drawing with respect to a substantially central position of the support member 140 in the plane direction. As shown in FIG. 14B, a step 252 is formed at a boundary between an end portion 251 of the projection 240A on a distal side in an extending direction and the first region 141 of the support member 140. The step 252 has a size that does not cause a decrease in visibility. Further, the size is to the extent that an unexpected behavior does not occur when the inflatable member 130 is depressurized. Other configurations are similar as those of the projection 240 of the embodiment.

As shown in FIG. 15A, a projection 240B of the second modification has a gentle mountain shape in the plan view. In the plan view, an arc of the projection 240B extends close to the inner peripheral edge of the one first hole portion 145a. The projection 240B is disposed on an upper side in the drawing with respect to the substantially central position of the support member 140 in the plane direction. As shown in FIG. 15B, a step 254 is formed at a boundary between an end portion 253 of the projection 240B on a distal side in an extending direction and the first region 141 of the support member 140. Similarly to the projection 240A of the first modification, the step 254 has a size that does not cause a decrease in visibility. Further, the size is to the extent that an unexpected behavior does not occur when the inflatable member 130 is depressurized. Other configurations are similar as those of the projection 240 of the embodiment.

As shown in FIG. 16A, a projection 240C of the third modification has a mountain shape on the third band 170 side and a rectangular shape on an opposite side in the plan view. In the plan view, an arc of the projection 240C extends close to the inner peripheral edge of the one first hole portion 145a. Similarly to the projection 240 of the embodiment, the projection 240C extends from the third band 170 side of the first region 141 to the center point R side of the first region 141, and a thickness of the projection 240C decreases from the third band 170 side of the first region 141 to the center point R side of the first region 141. The projection 240C extends beyond the substantially central position of the support member 140 in the plane direction to a vicinity of the other first hole portion 145b on a lower side in the drawing. As shown in FIG. 16B, a step 256 is formed at a boundary between an end portion 255 of the projection 240C on a distal side in an extending direction and the first region 141 of the support member 140. Similarly to the projection 240A of the first modification, the step 256 has a size that does not cause a decrease in visibility. Further, the size is to the extent that an unexpected behavior does not occur when the inflatable member 130 is depressurized. Other configurations are similar as those of the projection 240 of the embodiment. The projection 240C of the third modification is larger than the projection 240 of the embodiment. Therefore, an external shape of the hemostatic device 100 (in particular, external shape of pressing member 110) becomes slightly bulky. Since the marker 135 overlaps the projection 240C, the fit feeling when the hemostatic device 100 is attached to the patient is also slightly reduced. However, since a range of the projection 240C on the support member 140 is large, an area of an inner surface of the projection 240C coming into contact with the inflatable member 130 is relatively large, and the inflatable member 130 can be effectively pressed. Accordingly, when the support member 140 is inclined, the compressing direction of the pressing portion is directed to the direction toward the puncture site p1 with a limited amount of deviation from the direction toward the puncture site p1.

As shown in FIG. 17A, a projection 240D of the fourth modification has an arc similar to that of the one first hole portion 145a in the plan view. As shown in FIG. 17B, the projection 240D of the fourth modification also extends from the third band 170 side of the first region 141 to the center point R side of the first region 141, and a thickness of the projection 240D decreases from the third band 170 side of the first region 141 to the center point R side of the first region 141. A relatively large step 258 is formed at a boundary between an end portion 257 of the projection 240D on a distal side in an extending direction and the first region 141 of the support member 140. The step 258 is formed near the one first hole portion 145a and is present at a position relatively separated from the marker 135. Therefore, the step 258 does not cause a decrease in visibility. Other configurations are similar as those of the projection 240 of the embodiment.

Figure 11C:
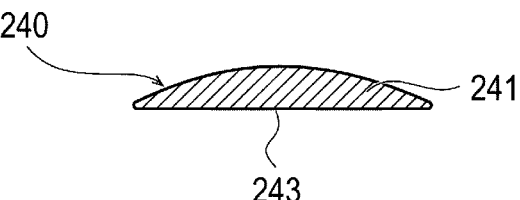
FIG. 11C is an end surface view showing a cross-sectional shape of a projection of the support member taken along a line XIC-XIC in FIG. 11A.
Figure 18:
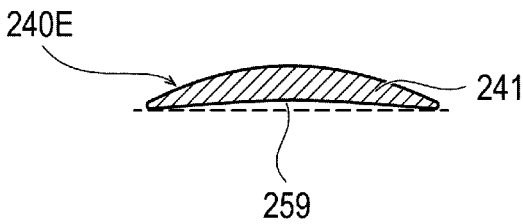
FIG. 18 is an end surface view showing a cross-sectional shape of a projection of the support member according to a fifth modification and is an end surface view corresponding to FIG. 11C.

FIG. 18 is an end surface view showing a cross-sectional shape of a projection 240E of the support member 140 of a fifth modification and is an end surface view corresponding to FIG. 11C. As shown in FIG. 18, the projection 240E of the fifth modification has an inner surface 259 located in the direction of facing the pressing portion 120. As shown in FIG. 18, the inner surface 259 of the projection 240E can have a shape in which a cross section in a direction intersecting with a direction in which the third band 170 extends is curved in a concave shape away from the pressing portion 120.

The "direction in which the third band 170 extend" is the upper-lower direction in FIG. 12A. For convenience of description, the direction in which the third band 170 extends is also referred to as a "vertical direction", and the direction intersecting the direction in which the third band 170 extends is also referred to as a "horizontal direction". "Away from the pressing portion 12" is away from the surface of the hand H of the patient (upper side in FIG. 27) when the hemostatic device 100 is attached to the hand H of the patient.

Since a cross-sectional shape of the inner surface 259 of the projection 240E is curved in a concave shape in the horizontal direction, the pressing portion 120 can be effectively pressed not only from one side in the vertical direction but also from the horizontal direction. Accordingly, when the support member 140 is inclined, the compressing direction of the pressing member 110 is directed to the direction toward the puncture site p1 with a limited amount of deviation from the direction toward the puncture site p1. Other configurations are similar as those of the projection 240 of the embodiment.

Figure 19A:
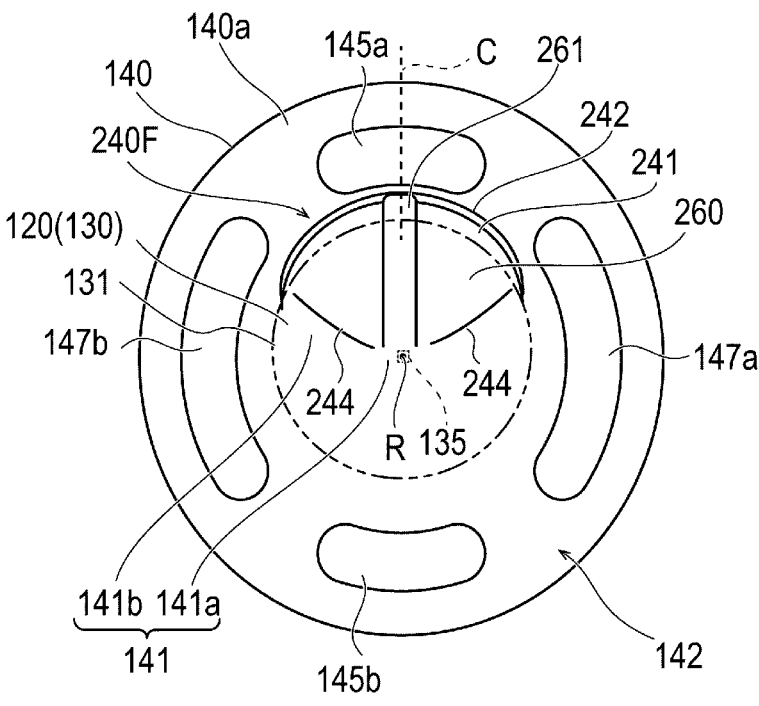
FIG. 19A is a plan view of the support member according to a sixth modification viewed from the one surface side on which the pressing portion is disposed.
Figure 19B:
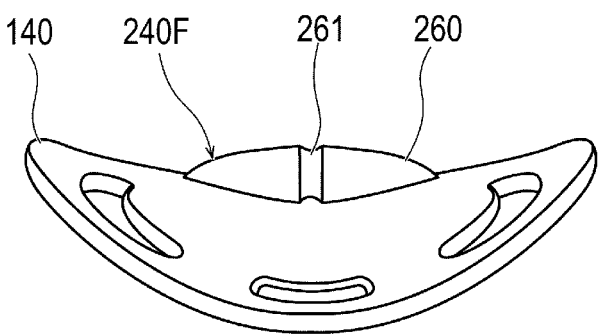
FIG. 19B is a perspective view of the support member according to a sixth modification viewed from a proximal side (forearm portion side).

As shown in FIGS. 19A and 19B, a projection 240F of a sixth modification has an inner surface 260 located in a direction of facing the pressing portion 120. The inner surface 260 of the projection 240F can have one guide groove 261 configured to hold a part of an elongated medical device (for example, sheath tube 201 of introducer 200) indwelt in the puncture site p1. Other configurations are similar as those of the projection 240 of the embodiment.

The guide groove 261 has an elongated groove shape capable of holding, for example, an external peripheral surface of the sheath tube 201 (corresponding to sheath) of the introducer 200 (see FIGS. 22 and 23). A cross-sectional shape of the guide groove 261 is not particularly limited, and can be a semi-arc shape or a rectangular shape. The guide groove 261 can match, for example, the direction in which the major axis C of the third band 170 extends.

The projection 240F includes the guide groove 261 on the inner surface 260 of the projection 240F. Therefore, when the operator disposes the hemostatic device 100 at the puncture site p1 of the patient with the sheath tube 201 indwelt in the puncture site p1, the operator can dispose the hemostatic device 100 such that the sheath tube 201 matches the guide groove 261. Therefore, when disposing the hemostatic device 100 at the puncture site p1 of the patient, the operator can dispose the hemostatic device 100 so as to fit the surface of the hand of the patient. The operator can rather easily remove the sheath tube 201 along the guide groove 261 when the hemostatic device 100 is disposed at the puncture site p1 of the patient and the sheath tube 201 is removed during inflation of the inflatable member 130.

Figures 20A, 20B:
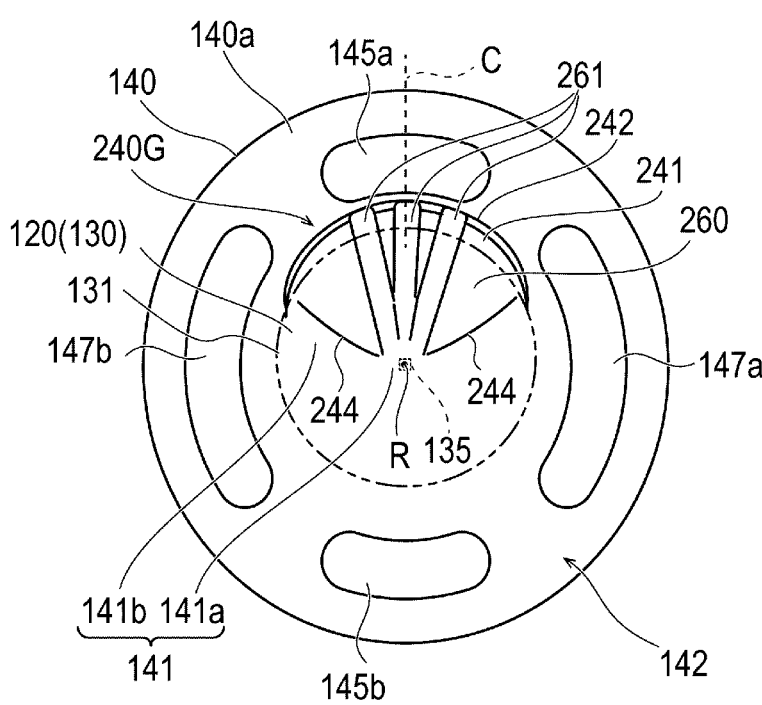
FIG. 20A is a plan view of the support member according to a seventh modification viewed from the one surface side on which the pressing portion is disposed.
FIG. 20B is a perspective view of the support member according to a seventh modification viewed from the proximal side (forearm portion side).

As shown in FIGS. 20A and 20B, a projection 240G of a seventh modification is different from the projection 240F of the sixth modification in that three guide grooves 261 are provided. Other configurations are similar as those of the projection 240F of the sixth modification and the projection 240 of the embodiment. When a position of the puncture point, a size or a shape of the hand, or the like is different, a position or an orientation of the sheath tube 201 is also different. In such a case, by providing the plurality of guide grooves 261, the guide groove 261 to be used can be selected. Therefore, when the operator disposes the hemostatic device 100 at the puncture site p1 of the patient with the sheath tube 201 indwelt in the puncture site p1, the operator can dispose the hemostatic device 100 such that the sheath tube 201 matches the guide groove 261 in accordance with the orientation of the sheath tube 201 indwelt in the puncture site p1. Therefore, when disposing the hemostatic device 100 at the puncture site p1 of the patient, the operator can further easily dispose the hemostatic device 100 so as to fit the surface of the hand of the patient.

As described above, the projections 240F and 240G of the sixth and seventh modifications can have the inner surface 260 located in the direction of facing the pressing portion 120, and the inner surface 260 of the projections 240F and 240G can have at least one guide groove 261 configured to hold a part of the elongated medical device.

According to the hemostatic device 100 configured as described above, the pressing portion 120 is implemented by the inflatable member 130, and the projections 240F and 240G include the guide groove 261 configured to hold a part of the elongated medical device (for example, sheath tube 201) on the inner surfaces of the projections 240F and 240G. Therefore, when the operator disposes the hemostatic device 100 at the puncture site p1 of the patient with the sheath tube 201 indwelt in the puncture site p1, the operator can dispose the hemostatic device 100 such that the sheath tube 201 matches the guide groove 261. Therefore, when disposing the hemostatic device 100 at the puncture site p1 of the patient, the operator can dispose the hemostatic device 100 so as to fit the surface of the hand of the patient. The operator can rather easily remove the sheath tube 201 along the guide groove 261 when the hemostatic device 100 is disposed at the puncture site p1 of the patient and the sheath tube 201 is removed during inflation of the inflatable member 130. When a plurality of guide grooves 261 are provided, the operator can select the guide groove 261 in accordance with the orientation of the elongated medical device indwelt in the puncture site p1. Therefore, when disposing the hemostatic device 100 at the puncture site p1 of the patient, the operator can further easily dispose the hemostatic device 100 so as to fit the surface of the hand of the patient.

The hemostatic device according to the disclosure has been described above through the embodiment, but the disclosure is not limited to the contents described in the specification, and can be appropriately changed based on the description of the claims.

In the description of the embodiment, the hemostatic device including the configuration in which the first band and the second band are configured to slide about the center point of the support member and the third band is configured not to slide about the center point of the support member is described. The hemostatic device may have a configuration in which the third band is also slidable about the center point of the support member.

In the description of the embodiment, the support member 140 includes a total of four hole portions which are a pair of the first hole portions 145a and 145b and a pair of second hole portions 147a and 147b. The specific number of the hole portions can be appropriately changed. For example, the other first hole portion 145b of the pair of first hole portions 145a and 145b may not be provided, and a total of three hole portions may be provided.

In the description of the embodiment, the band is configured to slide about the center point of the support member in a state where the band is connected to the hole portion of the support member. A structure for connecting the band to the support member is not limited to the hole portion in the support member. The structure for connecting the band to the support member can also be implemented by, for example, a convex portion provided on one of the support member and the band, and a groove provided on the other of the support member and the band and slidably holding the convex portion.

In the description of the embodiment, the hemostatic device for stopping bleeding of the puncture site formed in the dorsal side of the hand is described. The hemostatic device can also be used to stop bleeding of a puncture site formed in a palm of the hand. An arrangement of the bands when the hemostatic device is attached to the patient is not limited to the positions shown in the drawings, and can be appropriately changed. For example, the third band may be disposed at an interdigital portion other than the interdigital portion located between the thumb and the forefinger. Similarly to the hand, the hemostatic device may be used for a foot having many moving portions such as toes, in the same way as the hand. For example, the hemostatic device may be used for stopping bleeding of a puncture site formed in a foot of the patient (for example, dorsum or sole).

A shape, dimensions, and the like of each part of the hemostatic device are not particularly limited as long as the inflatable member can be disposed at a site where bleeding is to be stopped, and can be appropriately changed.

The detailed description above describes embodiments of a hemostatic device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
a pressing member configured to compress a puncture site formed in a patient;
a first band configured to be connected to the pressing member;
a second band configured to be connected to the pressing member;
a third band configured to be connected to the pressing member;
the pressing member including an inflatable member configured to compress the puncture site and a support member configured to fix the pressing member;
the support member including a first region in which the pressing member is located, and a second region which is located outside the first region and to which the first band, the second band, and the third band are connectable;
the third band extending in a different direction from the first band and the second band in a state where the third band is connected to the second region;
wherein the support member includes a projection protruding toward the pressing member on a third band side of the first region;
wherein the projection extends from the third band side of the first region to a center point side of the first region; and
wherein a thickness of the projection decreases from the third band side of the first region toward the center point side of the first region.

2. The hemostatic device according to claim 1, wherein the projection has an inclined portion that extends from the third band side of the first region toward a central region located at a center of the first region and comes into contact with the pressing member;
the inflatable member is configured to be inflated by injecting a fluid, and
a thickness of the projection is larger than a thickness of the central region located at the center of the first region of the support member.

3. The hemostatic device according to claim 1, wherein the projection has an external shape bilaterally symmetrical with respect to a major axis of the third band.

4. The hemostatic device according to claim 1, wherein the inflatable member has a peripheral edge portion located at a peripheral edge of a portion that is configured to be inflated by injecting a fluid, and
a peripheral edge of the projection has a shape matching the peripheral edge portion of the inflatable member.

5. The hemostatic device according to claim 1, wherein the inflatable member is configured to be inflated by injecting a fluid,
the projection has an inner surface located in a direction of facing the pressing member, and
the inner surface of the projection has at least one guide groove configured to hold a part of an elongated medical device.

6. A hemostatic method comprising:
providing the hemostatic device of claim 1;
positioning the pressing member on the support member of the hemostatic device over the puncture site formed in the patient; and
attaching the pressing member on the support member of the hemostatic device to the patient with the first band, the second band, and the third band.

7. A hemostatic device comprising:
a pressing member configured to compress a puncture site formed in a patient;
a first band configured to be connected to the pressing member;
a second band configured to be connected to the pressing member;
a third band configured to be connected to the pressing member;
the pressing member including an inflatable member configured to compress the puncture site and a support member configured to fix the pressing member;
the support member including a first region in which the pressing member is located, and a second region which is located outside the first region and to which the first band, the second band, and the third band are connectable;
the third band extending in a different direction from the first band and the second band in a state where the third band is connected to the second region;
wherein the support member includes a projection protruding toward the pressing member on a third band side of the first region;
wherein the first region of the support member includes a central region located at a center of the first region and a curved region curved in a direction away from the pressing member from the central region toward a peripheral edge of the support member; and
the projection is located in the curved region, and at least a part of the projection protrudes to a pressing member side relative to the central region.

8. A hemostatic device comprising:
a pressing member configured to compress a puncture site formed in a patient;
a first band configured to be connected to the pressing member;
a second band configured to be connected to the pressing member;
a third band configured to be connected to the pressing member;

the pressing member including an inflatable member configured to compress the puncture site and a support member configured to fix the pressing member;

the support member including a first region in which the pressing member is located, and a second region which is located outside the first region and to which the first band, the second band, and the third band are connectable;

the third band extending in a different direction from the first band and the second band in a state where the third band is connected to the second region;

wherein the support member includes a projection protruding toward the pressing member on a third band side of the first region;

wherein the projection has an inner surface located in a direction of facing the pressing member; and the inner surface of the projection has a shape in which a cross section in a direction intersecting with a direction in which the third band extends is curved in a concave shape away from the pressing member.

\* \* \* \* \*